United States Patent [19]

Kinney

[11] Patent Number: 5,500,361
[45] Date of Patent: Mar. 19, 1996

[54] β-KETOACYL-ACP SYNTHETASE II GENES FROM PLANTS

[75] Inventor: Anthony J. Kinney, Wilmington, Del.

[73] Assignee: E. I. Du Pont de Nemours and Company, Wilmington, Del.

[21] Appl. No.: 232,079

[22] PCT Filed: Nov. 12, 1992

[86] PCT No.: PCT/US92/09733

§ 371 Date: May 10, 1994

§ 102(e) Date: May 10, 1994

[87] PCT Pub. No.: WO93/10240

PCT Pub. Date: May 27, 1993

Related U.S. Application Data

[63] Continuation-in-part of Ser. No. 791,921, Nov. 15, 1991, abandoned.

[51] Int. Cl.$^6$ .......................... C12N 15/29; C12N 15/82; C12N 5/14; A01H 5/00
[52] U.S. Cl. .................. 435/172.3; 435/69.1; 435/71.1; 435/240.4; 536/23.6; 800/205; 800/250; 800/255; 800/DIG. 69
[58] Field of Search .................................. 800/205, 250, 800/255; 536/23.6; 435/172.3, 69.1, 240.4, 71.1

[56] References Cited

U.S. PATENT DOCUMENTS

| | | | |
|---|---|---|---|
| 4,394,443 | 7/1983 | Weissman et al. | 435/6 |
| 5,057,419 | 10/1991 | Martin et al. | 435/134 |
| 5,110,728 | 5/1992 | Kridl et al. | 435/69.1 |

FOREIGN PATENT DOCUMENTS

| | | | |
|---|---|---|---|
| 0255378 | 2/1988 | European Pat. Off. | C12N 15/00 |
| WO91/13972 | 9/1991 | WIPO | C12N 1/21 |
| WO92/03564 | 3/1992 | WIPO | C12P 7/64 |

OTHER PUBLICATIONS

MacKintosh, R. W. et al, *Biochem. Biophys. Acta.*, 1002, 114–124 (1989).
Siggaard–Andersen, M. et al, *Proc. Natl. Acad. Sci. USA* 88, 4114–4118 (1991).
Bibb et al, *EMBO J.*, 8, 2727–2736 (1989).
Kauppinen et al., Poster Abstract No. 715,, 3rd Int'l. Congress of Plant Molecular Biology, Oct. 6–11, 1991.
Genez et al, Poster Abstract No. 719, 3rd Int'l. Congress of Plant Molecular Biology, Oct. 6–11, 1991.
Alberts, A. W. et al, *Biochemistry*, 4(11), 2265–2274 (1965).
D'Agnolo, G. et al, *J. Biol. Chem.*, 250(14), 5289–5294 (1975).
Garwin, J. L. et al, *J. Biol. Chem.*, 225(8), 3263–3265 (1980).
Garwin, J. L. et al, *J. Biol. Chem.*, 255(24), 11949–11956 (1980).
Greenspan, M. D. et al, *J. Biol. Chem.*, 244(23), 6477–6485 (1989).
Prescott, D. J. et al, *J. Biol. Chem.*, 245(20), 5485–5490 (1970).
Shimakata, T. *Proc. Nat'l. Acad. Sci*, 79, 5808–5812 (1982).
Somerville, C. et al, *Science*, 252, 80–87 (Apr. 5, 1991).
Kinney et al 9th Int'l Symposium on Plant Lipids, Portland Press (1990) Quinn et al (eds) pp. 126–128.
Knauf, *Trends in Biotech.*, 5, 40–47 (1987).
Battey, *Trends in Biotech*, 7, 122–126 (1989).
Slabas et al, In: Plant Molecular Biol. Proceedings, NATO ASI Series A, Life, Sci., Plenum Press, 140, 265–277 (1987).
Amy, et al, *Proc. Natl. Acad. Sci.*, 86, 3114–3118 (1989).
Mohamed et al, *J. Biol. Chem.*, 263, 12315–12325 (1988).
Kauppinen et al, *Carlsberg Res. Commun.*, 53, 357–370 (1988).
Shimakata, T. et al, *Plant Physiol.*, 79, 5808–5812 (1982).
Wilke–Douglas et al 1986 Physical Plantarum 68:560–565.

*Primary Examiner*—Patricia R. Moody

[57] ABSTRACT

The preparation and use of nucleic acid fragments encoding β-ketoacyl-ACP synthetase II enzyme or its precursor to modify plant oil composition are described. Chimeric genes incorporating such nucleic acid fragments and suitable regulatory sequences may be used to transform plants to control the levels of saturated and unsaturated fatty acids. Plants transformed with the chimeric genes, seeds and oil of such plants are also provided.

10 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2675 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Glycine max
        ( B ) STRAIN: Cultivar Wye
        ( C ) CELL TYPE: Cotyledon ( v i i ) IMMEDIATE SOURCE:
        ( A ) LIBRARY: cDNA to mRNA (B) CLONE: pC16i (xi) SEQUENCE DESCRIPTION: SEQ ID NO:1:

| | | | | | | |
|---|---|---|---|---|---|---|
| CCAAAAACCC | AAACCCTTGG | CGGCTGCGAG | ACCCGTTGTG | TTCTCTCTTC | TCTCTCTCTT | 60 |
| CTTTTTTTTT | TCTCTTTCCC | TCTCTTCTTC | GCTCCTTTTA | GGGTTTTCTC | AACTCTTCGA | 120 |
| TTTGGGGCTT | AAACCCTCTC | CGATTCAGAT | TCGGATTTAG | GGCTTCCCTT | TCTCTATTCC | 180 |
| GCCTCCAAAG | AAAAACAGAT | CTCGTGGTTG | GTTCGTCATG | GCCACCGTTG | CTAACCGCGG | 240 |
| ATCAGCAACT | GATTTGCTAC | AGAAGCTATC | GTTAGAAACT | CAGCCCAAGC | CCTTGGAGAT | 300 |
| TCCTGAGCCT | ACCAAAAAGC | CACTGGGGAA | TCAGTATGGA | TCAGTTGATT | CAGGAATGCC | 360 |
| GCGAATGCCA | GATCAGTCGT | ATGATCGGTC | TGTACTCCGT | GTTGCAGGAT | TTTATTTGAC | 420 |
| CCTACTATGT | GTTACCTCCC | AAATGGTTAC | CCATCTACTG | CCTATTATTA | CGGTGGTTAT | 480 |
| GATGGAACTG | GTAACGAGTG | GGATGAGTAT | CAAGATATGT | GAATTCGGAA | GGAGTGAGAT | 540 |
| GACTTCAGGA | GTTTATGGGG | ATAATGGGTC | TCTACTTTAT | CACCATGGAT | ATGGATATGC | 600 |
| GCCTTATGGC | CCCTATCGCC | CAGCAGGGTC | TCCAGTCCAA | CCATGGGGAA | TGATGGTCAG | 660 |
| TGATGGGCTC | AACACTATGC | TGTATCCTCC | ATACTCCTCC | GAACCGTTAA | CACCGAACCA | 720 |
| GCGCGCCAGT | CACACCTACT | CCTGCTGCCC | TACCTCAGTG | AGGTTTCCAC | CTCTGTTGCT | 780 |
| GCTGATCAAA | AGCCTCTTCC | TGTTGAAGCA | GCCAATGAAA | ATTCTAATGG | TGTCTCAAAT | 840 |
| GGTGGCAATG | CAAAAGGTCG | TGGTCCAACC | TCAGGTTATC | AGGATCCAAG | ATTTGGTTAT | 900 |
| GATGGAGTCG | CTCACCTATC | CCCTGGCTAG | ATCCCCACT | ATTTTCAGAT | GGGCAACCAA | 960 |
| GGCCTGTACA | AGCACAACCA | TCACTTCTTC | GATATCAGGT | GGCAACAACA | CTGCCTCAAG | 1020 |
| GAGCCAGACT | TTCCGCCCTA | ATTCTCAGTT | CATGGGCTTG | CACCACCCAA | GACCAATGCC | 1080 |
| TGCCATGGGA | GCCACCCATA | GCTTCATAAA | TAGGATGTAC | CCCAACAAAT | TATATGGTCA | 1140 |
| ATATGGGAAC | ACTGTCAGAT | CTGGAATGGG | TTATGGTACA | CATGGGTATG | ATTCTCGGGC | 1200 |
| TAATGGGCGG | GCTTGGTTGG | CTGTTGACAG | CAAATACAAA | ACTAGGGGAA | GAAGTGGTGG | 1260 |
| CTATTTTGGC | TATGGAAATG | AGAATGTAGA | TGGCTTGAAT | GAACTGAACA | GAGGCCCTAG | 1320 |
| GGCAAGGGTG | GCAAAAACCA | AAAGGTTTT | GCACCAACTA | TTTTGGCAGT | CAAAGGGCAG | 1380 |
| AACTTGCCTG | CAAGTAGGCA | CCGATGAAGA | GAAAGACAAG | ACTAGTACCG | TTCCGGACCG | 1440 |
| TGATCAGTAT | AACAAAGCTG | ATTTTCCAGA | AGAATATACT | GATGCTAAAT | TTTTTGTCAT | 1500 |
| CAAGTCTTAC | AGTGAGGATG | ATATCCATAA | GAGTATTAAG | TATAACGTGT | GGGCCAGTAC | 1560 |
| CCAAAATGGC | AACAAGAAGC | TTGATGCTGC | ATATCATGAG | GCACAGCAGA | AACCTGGTGG | 1620 |
| CTGCCCTGTT | TTTCTCTTTT | TCTCAGTTAA | TACCAGTGGG | CAATTTGTGG | GGCTTGCTGA | 1680 |
| AATGATTGGT | CCTGTTGATT | TTAACAAGAG | TGTTGAGTAT | GGCAGCAAG | ACAAGTGGAA | 1740 |
| TGGCTGCTTT | CCTCTTAAGT | GGCACGTTGT | TAAGGATGTT | CCTAACAATT | TGTTGAGGCA | 1800 |
| CATTACCCTG | GATAACAATG | AGTACAAACC | TGTCACTAAC | AGTAGGGATA | CACAAGAGGT | 1860 |
| AATGTTGGAG | CCTGGCCTGA | AATTAATCAA | AATTTTCAAG | GAATATACCA | CAAAGACATG | 1920 |
| CATTCTGGAT | GATTTTGGCT | TCTATGAGGC | CCGTCAGAAG | ACTATTTGG | AGAAGAAAGC | 1980 |
| AAAGCAACAA | TTCCCAAAGC | AGGTATGGGA | AGGGAAACCT | GCTGATGAGA | AGATTGAGAT | 2040 |
| AAATGGGGAA | GTCATACTCA | AAAATCTGAA | GTTAGCTCGG | AAGTGCTCAA | GGAGTCCCTT | 2100 |
| GCTGAGAAGG | ATAGTGATGA | CCACAAAGTT | CCCGAGAATG | GATGTGCTAC | AAAAACCTGG | 2160 |
| AGATGCCCCA | AAGGGTGCTA | AACCAGTTGT | TCCTGAGAGC | AAGATTGTAG | CCAATGGGGT | 2220 |
| TGTTTCTAAT | GGTTGCTAAG | CTCTACTGTG | TTTGAAGGAG | GCGGTCCTAT | CCATTTCAGT | 2280 |

```
GGCATATATT  GGTTCTTAGA  AGTATTTTAT  CAGAAACTTG  GTACCGCCTG  ATTTTATCTT      2340

TCTTGCCTCT  TCTCTTGCAG  TCTGAAGATA  GAGATTGGTT  GCCTAGTGAA  GATAAAGATC      2400

TGTATATTGA  GATTGGCTGG  GCGGAGTTAC  TTCATAGAAT  GCTAGCACCA  ATCCCTTCTC      2460

ATTGGGTTTT  GTTTACAGTG  GTTAGCTCCT  AACAGGCTTT  ACTCCTAGGG  TTTTTGGGT       2520

TTTAGGGTTT  CTGCCTAAGA  TGCTTATATC  TTTTGGTTTT  TGTTCGGGTT  TATCCTTCTC      2580

TTTGCCTTTT  TTCTTTTTTC  TTTCTTTTAT  TTTACTTTGT  TGGTCGTTTC  CTGTCTTGTA      2640

AATTTAGATC  TACTTTGTTG  CAGAGCAAAA  AAAAA                                   2675
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
          Val  Ile  Leu  Lys  Asn  Leu  Lys  Leu  Xaa  Tyr  Ser
          1                   5                        10
```

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GTNATHYTNA  ARAAYYTNAA  RT                                                    22
```

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: modified_base
        ( B ) LOCATION: 3
        ( C ) IDENTIFICATION METHOD: experimental
        ( D ) OTHER INFORMATION: /evidence=
            EXPERIMENTAL
            / mod_base=i ( i x ) FEATURE:
        ( A ) NAME/KEY: modified_base
        ( B ) LOCATION: 18
        ( C ) IDENTIFICATION METHOD: experimental
        ( D ) OTHER INFORMATION: /evidence=
            EXPERIMENTAL
            / mod_base=i ( x i ) SEQUENCE DESCRIPTION: SEQ ID NO:4:

```
GTNATHCTYA  ARAAYYTNAA  RT                                                    22
```

( 2 ) INFORMATION FOR SEQ ID NO:5:

( i ) SEQUENCE CHARACTERISTICS:
        ( A ) LENGTH: 22 base pairs (B) TYPE: nucleic acid
(C) STRANDEDNESS: single
(D) TOPOLOGY: linear (ii) MOLECULE TYPE: cDNA (ix) FEATURE:
(A) NAME/KEY: modified_base
(B) LOCATION: 3
(C) IDENTIFICATION METHOD: experimental
(D) OTHER INFORMATION: /evidence=
EXPERIMENTAL
/ mod_base=i (ix) FEATURE:
(A) NAME/KEY: modified_base
(B) LOCATION: 18
(C) IDENTIFICATION METHOD: experimental
(D) OTHER INFORMATION: /evidence=
EXPERIMENTAL
/ mod_base=i (xi) SEQUENCE DESCRIPTION: SEQ ID NO:5:

GTNATHTTRA ARAAYYTNAA RT    22

β-KETOACYL-ACP SYNTHETASE II GENES FROM PLANTS

This is a application is a continuation-in-part of Ser. No. 07/791,921, filed Nov. 15, 1991 (now abandoned).

FIELD OF THE INVENTION

The invention relates to the preparation and use of nucleic acid fragments encoding β-ketoacyl-ACP synthetase II enzyme or its precursor to modify plant oil composition. Chimeric genes incorporating such nucleic acid fragments and suitable regulatory sequences may be used to transform plants to control the levels of saturated and unsaturated fatty acids.

BACKGROUND OF THE INVENTION

Many recent research efforts have examined the role that saturated and unsaturated fatty acids play in reducing the risk of coronary heart disease. In the past, it was believed that monounsaturates, in contrast to saturates and polyunsaturates, had no effect on serum cholesterol and coronary heart disease risk. Several recent human clinical studies suggest that diets high in monounsaturated fat and low in saturated fat may reduce the "bad" (low-density lipoprotein) cholesterol while maintaining the "good" (high-density lipoprotein) cholesterol (Mattson et al. Journal of Lipid Research, (1985) 26:194–202; herein incorporated by reference).

Vegetable oils may play an important role in shifting the balance towards production of "good" cholesterol. The specific performance and health attributes of edible oils is determined largely by their fatty acid composition. Most vegetable oils derived from commercial varieties are composed primarily of palmitic (16:0), stearic (18:0), oleic (18:1), linoleic (18:2) and linolenic (18:3) acids. Palmitic and stearic acids are, respectively, 16- and 18-carbon-long, saturated fatty acids. Oleic, linoleic and linolenic are 18-carbon-long, unsaturated fatty acids containing one, two and three double bonds, respectively. Oleic acid is referred to as a monounsaturated fatty acid, while linoleic and linolenic acids are referred to as polyunsaturated fatty acids.

The relative amounts of saturated and unsaturated fats in commonly used edible vegetable oils are summarized below (Table 1):

TABLE 1

Percentages of Saturated and Unsaturated Fatty Acids in the Oils of Selected Oil Crops

|  | Saturated | Monounsaturated | Polyunsaturated |
| --- | --- | --- | --- |
| Canola | 6% | 58% | 36% |
| Soybean | 15% | 24% | 61% |
| Corn | 13% | 25% | 62% |
| Peanut | 18% | 48% | 34% |
| Safflower | 9% | 13% | 78% |
| Cotton | 30% | 19% | 51% |

A vegetable oil low in total saturates and high in monounsaturate would provide significant health benefits to consumers as well as economic benefits to oil processors. Soybean and corn varieties which produce seeds containing such an improved oil would also produce valuable meal as animal feed.

Another type of desirable vegetable oil is a substitute for palm oil and its fractionation products. Palm oil is the world's second most important vegatable oil, after soybean oil (Gascon et al., Oil Palm, In Oil Crops of the World, Robbelen et al., Ed., (1989) McGraw-Hill, Chapter 27). About 80% of the world palm oil is supplied by Malaysia and Indonesia, the remainder coming from Africa and South America. Palm oil is widely used in the manufacture of hardened vegetable fats such as margarines and shortenings. Palm stearin, about 10% of the palm oil, is used as a hardstock to increase the creaming properties of margarine blends and whipped toppings (Traitlet et al., J. Amer. Oil Chemists Soc., (1985) 62:417–421). Both palm oil and palm stearin have well-known non-food uses in the manufacture of soaps and lubricating oils. Palm olein (60% of the oil) is useful for cocking oils and interesterification of palm stearin with palm olein provides a hardstock for spread formulations without the use of hydrogenated fat components. Finally, the Palm Mid-Fraction (PMF), which is palm oil minus the palm stearin and palm olein fractions, is suitable for the manufacture of cocoa-butter substitutes (Traitler et al., J. Amer. Oil Chemists Soc., (1985), 62:417–421). Commercial palm oil con,sins 44% palmitate (P), 4.5% stearate (S) and 39.2% oleate (O) (Gunstone et al., The Lipid Handbook, Chapman-Hall, (1986) 176). Palm stearin (47–74% P, 4.4–5.6% S, 15.6–37% O), palm olein (39.8% P, 4.4% S, 42.5% O) and PMF (43% P, 5.6% S, 24.3% O) are produced by fractionation of palm oil (Gunstone et al., The Lipid Handbook, Chapman-Hall, (1986) 178). Thus, a vegetable oil, such as soybean, with an increased level palmitic acid, especially in oilseed lines containing suitable levels of oleic acid and reduced levels of unsaturated fatty acids, could yield a substitute for palm oil. Such a soybean or other oil seed could also yield a substitute for palm stearin, clein and PMF without the need for costly fractionation procedures. This would add value to oil and food processors as well as reduce the foreign import of palm oil.

Oil biosynthesis in plants has been fairly well-studied (Browse et al., Ann. Rev. Plant Physiol. Mol. Biol. (1991) 42: 467–506; Science (1991) 252:80–87)), From these studies it is apparent that in seed tissue the rate-limiting step in the metabolism of palmitic acid to stearic acid and the subsequent formation of oleic acid is the reaction catalyzed by the enzyme β-ketoacyl-ACP synthetase II. Thus, β-ketoacyl-ACP synthetase II is an attractive target for modification by genetic engineering since a decrease in β-ketoacyl-ACP synthetase II activity would presumably lead to an increased palmitic acid content of the plant oil and an increase in β-ketoacyl-ACP synthetase II activity would presumably lead to higher unsaturated fatty acids at the expense of saturated fats in the oil.

No evidence exists in the public art that complete isolation of a plant β-ketoacyl-ACP synthetase II has been accomplished. The partial purification of a β-ketoacyl-ACP synthetase II was reported from spinach leaves (Shimakata et al., Proc. Natl. Acad. Sci. (1982) 79:5808–5812) and oilseed rape (MacKintosh et al., Biochim. Biophys. Acta. (1989) 1002:114–124) but in neither case was the purification sufficient to identify a single protein associated with β-ketoacyl-ACP synthetase II activity. Furthermore, there is no evidence that a method to control the levels of saturated and unsaturated fatty acids in edible plants is known in the art.

SUMMARY OF THE INVENTION

A means to control the levels of saturated and unsaturated fatty acids in edible plant oils has been discovered. Utilizing β-ketoacyl-ACP synthetase II cDNAs for either the precursor or enzyme, chimeric genes are created and may be utilized to transform various plants to modify the fatty acid composition of the oil produced. Specifically, one embodiment of the invention is an isolated nucleic acid fragment comprising a nucleotide sequence encoding a plant β-ketoacyl-ACP synthetase II. The plant in this embodiment may more specifically be soybean, oilseed Brassica species, sunflower, *Arabidopsis thaliana*, cotton, tomato and tobacco. Another aspect of the present invention is a nucleic acid fragment comprising a nucleotide sequence encoding the soybean seed β-ketoacyl-ACP synthetase II cDNA corresponding to nucleotides 1 to 2676 in the sequence shown in SEQ ID NO:1, or any nucleic acid fragment substantially homologous therewith. Additional embodiments are those nucleic acid fragments encoding the soybean seed β-ketoacyl-ACP synthetase II precursor (nucleotides 218–2675 of SEQ ID NO:1) or the mature soybean seed β-ketoacyl-ACP synthetase II enzyme (nucleotides 311–2675 of SEQ ID NO:1).

Another aspect of this invention involves a chimeric gene capable of transforming a soybean plant cell comprising a nucleic acid fragment encoding soybean seed β-ketoacyl-ACP synthetase II cDNA operably linked to suitable regulatory sequences, the chimeric gene causing altered levels of seed β-ketoacyl-ACP synthetase II in the seed. Additional embodiments are those chimeric genes which incorporate nucleic acid fragments encoding soybean β-ketoacyl-ACP synthetase II synthase precursor (nucleotides 218–2675 of SEQ ID NO:1) or mature soybean seed β-ketoacyl-ACP synthetase II enzyme (nucleotides 311–2675 of SEQ ID NO:1).

Yet another embodiment of the invention involves a method of producing seed oil containing altered levels of saturated and unsaturated fatty acids comprising: (a) transforming a plant cell with a chimeric gene described above, (b) growing sexually mature plants from the transformed plant cells of step (a), (c) screening progeny seeds from the sexually mature plants of step (b) for the desired levels of palmitic, stearic and oleic acid, and (d) crushing the progeny seed of step (c) to obtain seed oil containing altered levels of palmitic, stearic and oleic acid. Preferred plant cells and oils are derived from soybean, rapeseed, sunflower, cotton, cocoa, peanut, safflower, and corn. Preferred methods of transforming such plant cells would include the use of Ti and Ri plasmids of Agrobacterium, electroporation, and high-velocity ballistic bombardment.

The invention also is embodied in a method of RFLP breeding to obtain altered levels of palmitic, stearic and oleic acids in seed oil. This method involves (a) making a cross between two varieties of soybean differing in the trait; (b) making a Southern blot of restriction enzyme digested genomic DNA isolated from several progeny plants resulting from the cross; and (c) hybridizing the Southern blot with the radiolabelled nucleic acid fragment of nucleotides 311–2675 of SEQ ID NO:1, or any nucleic acid fragment at least 90% identical to it.

The invention is also embodied in oilseed plants transformed with a chimeric gene comprising a nucleic acid fragment comprising nucleotides 311–2675 of SEQ ID NO:1 operably linked to suitable heterologous regulatory sequences, the chimeric gene causing altered levels of seed β-ketoacyl-ACP synthetase II in a seed produced by the transformed plant.

A further embodiment is the seed of an oilseed plant transformed with the chimeric gene. Another embodiment of the invention is the oil produced by the seed of an oil seed plant transformed with the chimeric gene.

BRIEF DESCRIPTION OF THE SEQUENCE DESCRIPTIONS

The invention can be more fully understood from the following detailed description and the Sequence Descriptions which form a part of this application. The Sequence Descriptions contain the three letter codes for amino acids as defined in 37 C.F.R. 1.822 which are incorporated herein by reference.

SEQ ID NO:1 shows the nucleotide sequence of a soybean seed β-ketoacyl-ACP synthetase II cDNA (pC16i). The nucleotide sequence of 2675 base pairs reads from 5' to 3'. In SEQ ID NO:1, nucleotide 1 is the first nucleotide of the Eco RI cut site reading from 5' to 3' on the cDNA insert and nucleotide 2675 is the last nucleotide of the cDNA insert in the Eco RI cut site of plasmid pC16i which encodes the soybean seed β-ketoacyl-ACP synthetase II. Nucleotides 218 to 220 are the putative translation initiation codon, nucleotides 311 to 313 are the codon for the putative N-terminal of the mature enzyme, nucleotides 2181 to 2183 are the termination codon, nucleotides 1 to 310 are the 5' untranslated sequence and nucleotides 2184 to 2675 are the 3' untranslated nucleotides.

SEQ ID NO:2 shows a partial amino acid sequence of purified soybean β-ketoacyl-ACP synthetase II.

SEQ ID NO:3 shows a 22 nucleotide long oligomer from SEQ ID NO:2 above from which probes were developed.

SEQ ID NO:4 and SEQ ID NO:5 represent a series of degenerate probes used for hybridization.

DETAILED DESCRIPTION OF THE INVENTION

Applicants have isolated a nucleic acid fragment that encodes a β-ketoacyl-ACP synthetase II and is useful in controlling the composition of fatty acids in oilseed crops.

The biosynthesis of palmitic, stearic and oleic acids occurs in the plastids of plant cells by the interplay of three key enzymes of the "ACP track": β-ketoacyl-ACP synthetase II, stearoyl-ACP desaturase and acyl-ACP thioesterase. In seed tissue, the formation of oleoyl-ACP appears not to be limited by stearoyl-ACP desaturase but by the formation of the substrate for this enzyme, stearoyl-ACP (Post-Beittenmiller et al., J. Biol. Chem. (1991) 266:1858–1865). The rate-limiting step in the synthesis of stearoyl-ACP from palmitoyl-ACP is catalyzed by the enzyme β-ketoacyl-ACP synthetase II (Nagi et al., Anal. Biochem. (1989) 179:251–261). The other enzyme, acyl-ACP thioesterase, functions to remove the acyl chain from the carrier protein (ACP) and thus from the metabolic pathway. The same enzyme, with slightly differing efficiency, catalyzes the hydrolysis of the palmitoyl, stearoyl and oleoyl-ACP thioesters. This multiple activity leads to substrate competition between enzymes and it is the competition of acyl-ACP-thioesterase and β-ketoacyl-ACP synthetase II for the same substrate and of acyl-ACP thioesterase and stearoyl-ACP desaturase for the same substrate that leads to the production of a particular ratio of palmitic, stearic and oleic acids. An increase in β-ketoacyl-ACP synthetase II activity would result in an increased formation of stearoyl-ACP and a decreased amount of palmitoyl-ACP being removed from the "ACP-track" by the thioesterase. A decrease in β-ketoacyl-ACP synthetase II activity would result in an increased formation of palmitoyl- ACP and an increased removal of palmitoyl-ACP from the ACP-track.

Once removed from the ACP track by the action of acyl-ACP thioesterase, fatty acids are exported to the cytoplasm and used there to synthesize acyl-coenzyme A (CoA). These acyl-CoA's are the acyl donors for at least three different glycerol acylating enzymes (glycerol-3-P acyltransferase, 1-acyl-glycerol-3-P acyltransferase and diacylglycerol acyltransferase) which incorporate the acyl moieties into triacylglycerides during oil biosynthesis.

These acyltransferases show a strong, but not absolute, preference for incorporating saturated fatty acids at positions 1 and 3 and monounsaturated fatty acid at position 2 of the triglyceride. Thus, altering the fatty acid composition of the acyl pool will drive by mass action a corresponding change in the fatty acid composition of the oil. Furthermore, there is experimental evidence that, because of this specificity, and given the correct composition of fatty acids, plants can produce cocoa butter substitutes (Bafor et al., J. Amer. Oil Chemists Soc., (1990) 67:217–225).

Based on the above discussion, one approach to altering the levels of palmitic, stearic and oleic acids in vegetable oils is by altering their levels in the cytoplasmic acyl-CoA pool used for oil biosynthesis. It is possible to genetically modulate the competition between β-ketoacyl-ACP synthetase II and acyl-ACP thioesterase by modulating the expression level of β-ketoacyl-ACP synthetase II. Increasing the level of β-ketoacyl-ACP synthetase II activity would result in an increased synthesis of stearoyl-ACP and, since this substrate is limiting the in vivo stearoyl-ACP desaturase activity, would also result in an increased level of oleoyl-ACP. The likely result would be a reduction in the palmitic acid content of the soybean oil and an increased oleic acid content. In a like but opposite manner, decreasing β-ketoacyl-ACP synthetase II activity and so increasing palmitoyl-ACP would result in increased levels of palmitic acid in soybean oil. Increased activity of β-ketoacyl-ACP synthetase II would result from overexpression of cloned and re-introduced synthase genes, while decreased β-ketoacyl-ACP synthetase II activity leading to increased total palmitic acid would result from expression of antisense message from the β-ketoacyl-ACP synthetase II gene or sense expression of a β-ketoacyl-ACP synthetase II cDNA which is homologous to the endogenous gene (cosuppression).

Thus, transfer of the nucleic acid fragment of the invention or a part thereof that encodes a functional enzyme, along with suitable regulatory sequences into a living cell will result in the production or overproduction of β-ketoacyl-ACP synthetase II, which results in increased levels of stearic and oleic acids in cellular lipids, including oil.

Transfer of the nucleic acid fragment or fragments of the invention, along with suitable regulatory sequences that transcribe the present cDNA, into a plant which has an endogenous seed β-ketoacyl-ACP synthetase II that is substantially homogenous with the present cDNA may result in inhibition by cosuppression of the expression of the endogenous β-ketoacyl-ACP synthetase II gene and, consequently, in an increased amount of palmitic acid in the seed oil.

Transfer of the nucleic acid fragments of the invention into an oil-producing plant with suitable regulatory sequences that transcribe the antisense RNA complementary to the mRNA, or its precursor, for seed β-ketoacyl-ACP synthetase II may result in the inhibition of the expression of the endogenous β-ketoacyl-ACP synthetase II gene and, consequently, in an increased amount of palmitic acid in the seed oil.

The nucleic acid fragments of the invention can also be used as a restriction fragment length polymorphism (RFLP) markers in soybean genetic studies and breeding programs.

The nucleic acid fragment of the invention, or a piece of it as short as 20 base pairs, can also be used as a probe for additional β-ketoacyl-ACP synthetase II genes in soybean and other plant species. Two short pieces of the present fragment of the invention, as short as 15 base pairs each, can be used to amplify a longer piece of β-ketoacyl-ACP synthetase II DNA from soybean DNA or RNA by a polymerase chain reaction. The longer piece of β-ketoacyl-ACP synthetase II DNA generated could be used as a probe for additional β-ketoacyl-ACP synthetase II genes from soybean or other plant species.

DEFINITIONS

In the context of this disclosure, a number of terms shall be used. The term "nucleic acid" refers to a large molecule which can be single stranded or double stranded, composed of monomers (nucleotides) containing a sugar, a phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers. As used herein, the term "homologous to" refers to the complementarity between the nucleotide sequence of two nucleic acid molecules or between the amino acid sequences of two protein molecules. Estimates of such homology are provided by the comparison of sequence similarity between two nucleic acids or proteins. As used herein, "substantially homologous" refers to nucleic acid molecules which are at least 90% identical in their coding regions. "Related genes" refers to nucleic acids which have at least 50%, and more preferably 70%, nucleic acid sequence identity (WO 91/16421). "Related proteins" is used to mean at least 25% amino acid sequence identity between any two complete, mature proteins (see WO 91/16421 for discussion). The term "homologous β-ketoacylsynthetases" refers to β-ketoacylsynthetases (KASs) that catalyze the same condensation reaction on the same acyl-ACP substrate. Thus, KAS II enzymes (C16:0-ACP condensing enzymes), even from different plant species, are homologous β-ketoacylsynthetases. Homologous enzymes will have at least 50%, and more preferably 60%, amino acid sequence identity.

Thus, the nucleic acid fragments described herein include molecules which comprise possible variations of the nucleotide bases derived from deletion, rearrangement, random or controlled mutagenesis of the nucleic acid fragment, and even occasional nucleotide sequencing errors so long as the DNA sequences are substantially homologous.

"Gene" refers to a nucleic acid fragment that expresses a specific protein,-including regulatory sequences preceding (5' non-coding) and following (3' non-coding) the coding region. "β-ketoacyl-ACP synthetase II gene" refers to a nucleic acid fragment that expresses a protein with β-ketoacyl-ACP synthetase II activity. "Native" gene refers to the gene as found in nature with its own regulatory sequences. "Chimeric gene" refers to a gene that comprises heterogeneous regulatory and coding sequences. "Endogenous" gene refers to the native gene normally found in its natural location in the genome. A "foreign" gene refers to a gene not normally found in the host organism but that is introduced by gene transfer.

"Coding sequence" refers to a DNA sequence that codes for a specific protein and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is transcribed in the primary transcript but which is removed through cleavage and re-ligation of the RNA within the cell to create the mature mRNA that can be translated into a protein.

"Initiation codon" and "termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA) refers to the RNA that is without introns and that can be translated into protein by the cell. "cDNA" refers to a double-stranded DNA that is complementary to and derived from mRNA. "Sense" RNA refers to RNA transcript that include the mRNA. "Antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that may increase the efficacy of antisense RNA to block gene expression. "Ribozyme" refers to a catalytic RNA and includes sequence-specific endoribonucleases.

As used herein, "suitable regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell. In artificial DNA constructs regulatory sequences can also control the transcription and stability of antisense RNA.

"Promoter" refers to a DNA sequence in a gene, usually upstream (5') to its coding sequence, which controls the expression of the coding sequence by providing the recognition for RNA polymerase and other factors required for proper transcription. In artificial DNA constructs promoters can also be used to transcribe antisense RNA. Promoters may also contain DNA sequences that are involved in the binding of protein factors which control the effectiveness of transcription initiation in response to physiological or developmental conditions. It may also contain enhancer elements. An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Tissue-specific" or "development-specific" promoters as referred to herein are those that direct gene expression almost exclusively in specific tissues, such as leaves or seeds, or at specific development stages in a tissue, such as in early or late embryogenesis, respectively.

The term "expression", as used herein, is intended to mean the production of a functional end-product. Expression or overexpression of the β-ketoacyl-ACP synthetase II gene involves transcription of the gene and translation of the mRNA into precursor or mature β-ketoacyl-ACP synthetase II proteins. "Antisense inhibition" refers to the production of antisense RNA transcripts capable of preventing the expression of the target protein. "Overexpression" refers to the production of a gene product in transgenic organisms that exceeds levels of production in normal or non-transformed organisms. "Cosuppression" refers to the expression of a transgene which has substantial homology to an endogenous gene resulting in the suppression of expression of both the ectopic and the endogenous gene. "Altered levels" refers to the production of gene product (s) in transgenic organisms in amounts or proportions that differ from that of normal or non-transformed organisms.

The "3' non-coding sequences" refers to the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

"Mature" protein refers to a functional β-ketoacyl-ACP synthetase II enzyme without its transit peptide. "Precursor" protein refers to the mature protein with a native or foreign transit peptide. "Transit" peptide refers to the amino terminal extension of a polypeptide, which is translated in conjunction with the polypeptide forming a precursor peptide and which is required for its uptake by plastids of a cell.

"Transformation" herein refers to the transfer of a foreign gene into the genome of a host organism and its genetically stable inheritance. "Restriction fragment length polymorphism" refers to different sized restriction fragment lengths due to altered nucleotide sequences in or around variant forms of genes. "Fertile" refers to plants that are able to propagate sexually.

Purification of Soybean Seed β-ketoacyl-ACP synthetase II

In order to modulate the activity of β-ketoacyl-ACP synthethase II in the seed, it is essential to isolate or purify the complete gene(s) or cDNA(s) encoding the target enzyme(s).

β-ketoacyl-ACP synthetase II protein was purified to a single peptide when analyzed by SDS polyacrylamide gel electrophoresis (SDS-PAGE) starting from the soluble fraction of extracts made from developing soybean seeds (glycine max var. Wye) following binding to DEAE-cellulose, ammonium sulfate precipitation, chromatographic separation on blue sepharose, high performance anion exchange, alkyl-ACP sepharose, and phenyl-Superose. In a typical preparation, the fold purification of β-ketoacyl-ACP synthetase II activity was about 20,000. The preparation runs as a single band in native polyacrylamide gel electrophoresis and as a single, symmetrical peak in gel filtration chromatography indicating a native molecular weight of about 100

Antisense inhibition using the entire cDNA sequence has been shown. (Sheehy et al., Proc. Natl. Acad. Sci. USA (1988) 85:8805–8809). Thus, to express antisense RNA in soybean seed from the fragment of the invention, the entire fragment of the invention (that is, the entire cDNA for soybean β-ketoacyl-ACP synthetase II within the restriction sites described above) may be used. There is also evidence that the 3' non-coding sequences can play an important role in antisense inhibition (Ch'ng et al., Proc. Natl. Acad. Sci. USA (1989) 86:10006–10010) or short fragments of 5' coding sequence (as few as 41 base-pairs of a 1.87 kb cDNA) (Cannon et al., Plant Molec. Biol. (1990) 15:39–47). Thus, to express antisense RNA in soybean seed from the fragment of the invention, a small fragment of the invention, consisting of at least 41 base pairs of the β-ketoacyl-ACP synthetase II cDNA, may also be used.

Inhibition of Plant Target Genes by Cosuppression

The phenomenon of cosuppression has also been used to inhibit plant target genes in a dominant and tissue-specific manner (Napoli et al., The Plant Cell (1990) 2:279–289; van der Krol et al., The Plant Cell (1990) 2:291–299; Smith et al., Mol. Gen. Genetics (1990) 224:477–481). The nucleic acid fragment of the instant invention encoding soybean seed β-ketoacyl-ACP synthetase II cDNA, or a coding sequence derived from other cDNAs or genes for the enzyme, along with suitable regulatory sequences, can be used to reduce the level of the enzyme in a transgenic oilseed plant which contains an endogenous gene substantially homogenous to the introduced β-ketoacyl-ACP synthetase II cDNA. The experimental procedures necessary for this are similar to those described above for sense overexpression of the β-ketoacyl-ACP synthetase II cDNA. Cosuppressive inhibition of an endogenous gene using the entire cDNA sequence (Napoli et al., The Plant Cell (1990) 2:279–289; van der Krol et al., The Plant Cell (1990) 2:291–299) and also using part of a gene (730 bp of a 1770 bp cDNA) (Smith et al., Mol. Gen. Genetics (1990) 224:477–481) are known. Thus, all or part of the nucleotide sequence of the present β-ketoacyl-ACP synthetase II cDNA may be used to reduce the levels of β-ketoacyl-ACP synthetase II enzyme in a transgenic oilseed.

Selection of Hosts, Promoters and Enhancers

A preferred class of heterologous hosts for the expression of the coding sequence of β-ketoacyl-ACP synthetase II precursor or the antisense RNA are eukaryotic hosts, particularly the cells of higher plants. Particularly preferred among the higher-plants are the oilcrops, such as soybean (*Glycine max*), rapeseed (*Brassica napus, B. campestris*), sunflower (Helianthus annus), cotton (*Gossypium hirsutum*), corn (*Zea mays*), cocoa (*Theobroma cacao*), and peanut (*Arachis hypogaea*). Expression in plants will use regulatory sequences functional in such plants.

The expression of foreign genes in plants is well-established (De Blaere et al., Meth. Enzymol. (1987) 153:277–291). The origin of promoter chosen to drive the expression of the coding sequence or the antisense RNA is not critical provided it has sufficient transcriptional activity to accomplish the invention by increasing or decreasing, respectively, the level of translatable mRNA for β-ketoacyl-ACP synthetase II in the desired host tissue. Preferred promoters include (a) strong constitutive plant promoters, such as those directing the 19S and 35S transcripts in Cauliflower mosaic virus (Odell et al., Nature (1985) 313:810–812; Hull et al., Virology (1987) 86:482–493), and (b) tissue- or developmentally-specific promoters. Examples of tissue-specific promoters are the light-inducible promoter of the small subunit of ribulose 1,5-bisphosphate carboxylase if expression is desired in photosynthetic tissues, maize zein protein (Matzke et al., EMBO J. (1984) 3:1525), and chlorophyll a/b binding protein (Lampa et al., Nature (1986) 316:750–752).

Particularly preferred promoters are those that allow seed-specific expression. This may be especially useful since seeds are the primary source of vegetable oils and also since seed-specific expression will avoid any potential deleterious effect in non-seed tissues. Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al., Ann. Rev. Plant Physiol. (1984) 35:191–221; Goldberg et al., Cell (1989) 56:149–160). Moreover, different seed storage proteins may be expressed at different stages of seed development.

Expression of seed-specific genes has been studied in great detail (See reviews by Goldberg et al., Cell (1989) 56:149–160 and Higgins et al., Ann. Rev. Plant Physiol. (1984) 35:191–221). There are currently numerous examples for seed-specific expression of seed storage protein genes in transgenic dicotyledonous plants. These include genes from dicotyledonous plants for bean β-phaseolin (Sengupta-Gopalan et al., Proc. Natl. Acad. Sci. USA (1985) 82:3320–3324; Hoffman et al., Plant Mol. Biol. (1988) 11: 717–729), bean lectin (Voelker et al., EMBO J. (1987) 6:3571–3577), soybean lectin (Okamuro et al., Proc. Natl. Acad. Sci. USA (1986) 83:8240–8244), soybean Kunitz trypsin inhibitor (Perez-Grau et al., Plant Cell (1989) 1:095–1109), soybean β-conglycinin (Beachy et al., EMBO J. (1985) 3047–3053; pea vicilin (Higgins et al., Plant Mol. Biol. (1988) 11:683–695), pea convicilin (Newbigin et al., Planta (1990) 180:461), pea legumin (Shirsat et al., Mol. Gen. Genetics (1989) 215:326); rapeseed napin (Radke et al., Theor. Appl. Genet. (1988) 75:685–694) as well as genes from monocotyledonous plants such as for maize 15 kD zein (Hoffman et al., EMBO J. (1987) 6:3213–3221), maize 18 kD oleosin (Lee at al., Proc. Natl. Acad. Sci. USA (1991) 888:6181–6185), barley β-hordein (Marris et al., Plant Mol. Biol. (1988) 10:359–366) and wheat glutenin (Color et al., EMBO J. (1987) 6:3559–3564). Moreover, promoters of seed-specific genes operably linked to heterologous coding sequences in chimeric gene constructs also maintain their temporal and spatial expression pattern in transgenic plants. Such examples include *Arabidopsis thaliana* 2S seed storage protein gene promoter to express enkephalin peptides in Arabidopsis and *B. napus* seeds (Vandekerckhove et al., Bio/Technology (1989) 7:929–932), bean lectin and bean β-phaseolin promoters to express luciferase (Riggs et al., Plant Sci. (1989) 63:47–57), and wheat glutenin promoters to express chloramphenicol acetyl transferase (Color et al., EMBO J. (1987) 6:3559–3564).

Of particular use in the-expression of the nucleic acid fragment of the invention will be the heterologous promoters from several soybean seed storage protein genes such as those for the Kunitz trypsin inhibitor (Jofuku et al., Plant Cell (1989) 1: 1079–1093; glycinin (Nielson et al., Plant Cell (1989) 1:313–328), and β-conglycinin (Harada et al., Plant Cell (1989) 1:415–425). Promoters of genes for α- and β-subunits of soybean β-conglycinin storage protein will be particularly useful in expressing the mRNA or the antisense kD. SDS-PAGE of these preparations showed a peptide of about 55 kD. These results lead Applicants to the conclusion that the β-ketoacyl-ACP synthetase II has a peptide subunit of 55 kD which exists as a dimer in its native state.

Cloning of Soybean Seed β-ketoacyl-ACP synthetase II cDNA

The 55 kD peptide from HPLC gel filtration purification was desalted, lyophylized and used for N-terminal sequencing. The peptide gave the following amino acid sequence from its N-terminal: Val-Ile-Leu-Lys-Asn-Leu-Lys-Leu-Xaa-Tyr-Ser (SEQ ID NO:2). Based on the sequence from the first Val to the first two codons of the last Leu, a probe was made which consisted of a set of 192 degenerate 22-nucleotide long oligomers (SEQ ID NO:3). The probe, following radiolabeling, was used to screen a cDNA expression library made in Lambda Zap vector from poly $A^+$RNA from 20-day-old developing soybean seeds. Six positively-hybridizing plaques, which hybridized to both probes, were subjected to plaque purification. Sequences of the pBluescript (Stratagene) vector, including the cDNA inserts, from each of the purified phage stocks were excised in the presence of a helper phage and the resultant phagmids used to infect E. coli cells resulting in double-stranded plasmids, pC8, pC12, pC14, pC15A, pC16 and pC17. Plasmid pC16 was the largest of these plasmids. The soybean cDNA insert of 2.1 kB was excised, radiolabeled by random primer labeling and used to reprobe the same cDNA library. A clone, pC16i, was indentified which was 2.6 kB in size, was homologous with pC16 and contained extra nucleotides, absent in pC16, at the 5' end of the pC16i insert.

The cDNA insert in plasmid pC16i is flanked at both ends by the two Eco RI sites introduced by the cDNA construction and its cloning into the vector pBluescript. The nucleotide sequence of the cDNA insert in pC16i encodes a 672 amino acid open reading frame that includes the peptide sequence found in the purified protein at the 611th amino acid of the open reading frame. Since this sequence is not at the N-terminus it is assumed that the protein sequence, on which the probe design was based, was obtained from degraded 55 kD peptide. Based on homology with the N-termini of the E. coli and the barley synthetase I (50% similarity), the first amino acid of the mature protein is deduced as being the 31st. Thus the first 30 amino acids are presumably the transit peptide required for import of the precursor protein into the plastid. The methionine codon at base number 218 of pC16i is the apparent start methionine since: a) it is the first methionine after the last stop codons 5' to and inframe with the N-terminal sequence and, b) the N-terminal methionine in all but one known chloroplast transit peptides is followed by alanine. Thus, it can be deduced that the β-ketoacyl-ACP synthetase II precursor protein encoded by this gene consists of a 30 amino acid transit peptide and a 642 amino acid mature protein before any further proteolytic processing occurs. The insert of pC16i was cloned, in frame, into the expression vector pGEX-2T (Pharmacia) to give the plasmid pC16i-N5. When the cDNA in pC16i-N5 is expressed in E. coli, the resultant 80 kD fusion protein (26 kD glutathione-S-transferase and a 54 kD C16i protein) reacts specifically with rabbit antibodies raised against purified soybean β-ketoacyl-ACP synthetase II protein. In addition, antibodies raised in rabbits against the pC16i fusion protein preciptate β-ketoacyl-ACP synthetase II activity from developing soybean cell extracts.

A fragment of the instant invention may be used, if desired, to isolate substantially homologous β-ketoacyl-ACP synthetase II cDNAs and genes, including those from plant species other than soybean. Isolation of homologous genes is well-known in the art. Southern blot analysis reveals that the soybean cDNA for the enzyme hybridizes to several, different-sized DNA fragments in the genomic DNA of tomato, rapeseed (Brassica napus), soybean, sunflower and Arabidopsis thaliana (which has a very simple genome). Although the number of different genes or "pseudogenes" (nonfunctional genes) present in any plant is unknown, it is expected to be more than one since β-ketoacyl-ACP synthetase II is an important enzyme. Moreover, plants that are amphidiploid (that is, derived from two progenitor species), such as soybean, rapeseed (B. napus), and tobacco will have genes from both progenitor species.

Overexpression of the Enzyme in Transgenic Species

The nucleic acid fragment of the instant invention encoding soybean seed β-ketoacyl-ACP synthetase II cDNA, or a coding sequence derived from other cDNAs or genes for the enzyme, with suitable regulatory sequences, can be used to overexpress the enzyme in transgenic soybean as well as other transgenic species. Such a recombinant DNA construct may include either the native β-ketoacyl-ACP synthetase II gene or a chimeric gene. One skilled in the art can isolate the coding sequences from the fragment of the invention by using and/or creating sites for restriction endonucleases, as described in Sambrook et al. (Molecular Cloning, A Laboratory Manual, 2nd ed. (1989), Cold Spring Harbor Laboratory Press). For isolating the coding sequence of β-ketoacyl-ACP synthetase II precursor from the fragment of invention, an Nco I site can be engineered by substituting nucleotide A at position 323 with C and substituting nucleotide C at position 324 with A. More preferably, since there are other Nco I sites in the β-ketoacyl-synthetase II cDNA, a unique Sma I site can be engineered upstream of, and in frame with, the start methionine by inserting the three nucleotides CGG between nucleotides at position 180 and position 181. Cutting at these engineered sites along with cuts at restriction endonuclease sites near the 3' end of pC16i, such as the Kpn I site at position 2321, allows removal of the fragment encoding the β-ketoacyl-ACP synthetase II precursor protein and directional re-insertion into a properly designed vector.

Inhibition of Plant Target Genes by Use of Antisense RNA

Antisense RNA has been used to inhibit plant target genes in a dominant and tissue-specific manner (see van der Krol et al., BIOTECHNIQUES (1988) 6:958–976).

The use of antisense inhibition of the seed enzyme would require isolation of the coding sequence for genes that are expressed in the target tissue of the target plant. Thus, it will be more useful to use the fragment of the invention to screen seed-specific cDNA libraries, rather than genomic libraries or cDNA libraries from other tissues, from the appropriate plant for such sequences. Moreover, since there may be more than one gene encoding seed β-ketoacyl-ACP synthetase II, it may be useful to isolate the coding sequences from the other genes from the appropriate crop. The genes that are most highly expressed are the best targets for antisense inhibition. The level of transcription of different genes can be studied by known techniques, such as run-off transcription.

RNA to β-ketoacyl-ACP synthetase II in the cotyledons at mid- to late-stages of seed development (Beachy et al., EMBO J. (1985) 4:3047–3053 in transgenic plants. This is because there is very little position effect on their expression in transgenic seeds, and the two promoters show different temporal regulation. The promoter for the α-subunit gene being expressed a few days before that for the β-subunit gene. This is important for transforming rapeseed where oil biosynthesis begins about a week before seed storage protein synthesis (Murphy et al., J. Plant Physiol. (1989) 135:63–69).

Also of particular use will be promoters of genes expressed during early embryogenesis and oil biosynthesis. The native regulatory sequences, including the native promoter, of the β-ketoacyl-ACP synthetase II gene expressing the nucleic acid fragment of the invention can be used following its isolation by those skilled in the art. Heterologous promoters from other genes involved in seed oil biosynthesis, such as those for *B. napus* isocitrate lyase and malate synthase (Comai et al., Plant Cell (1989) 1:293–300), Arabidopsis ACP (Post-Beittenmiller et al., Nucl. Acids Res. (1989) 17:1777), *B. napus* ACP (Safford et al., Eur. J. Biochem. (1988) 174:287–295), *B. campestris* ACP (Rose et al., Nucl. Acids Res. (1987) 15:7197), and *Zea mays* oleosin (Lee et al., Proc. Natl. Acad. Sci. USA (1991) 88:6181–6185) may also be used. The genomic DNA sequence for *B. napus* oleosin is also published (Lee et al., Plant Physiol. (1991) 96:1395–1397) and one skilled in the art can use this sequence to isolate the corresponding promoter. The partial protein sequences for the relatively-abundant enoyl-ACP reductase and acetyl-CoA carboxylase are published (Slabas et al., Biochim. Biophys. Acta (1987) 877:271–280; Cottingham et al., Biochim. Biophys. Acta (1988) 954:201–207) and one skilled in the art can use these sequences to isolate the corresponding seed genes with their promoters.

Attaining the proper level of expression of β-ketoacyl-ACP synthetase II mRNA or antisense RNA may require the use of different chimeric genes utilizing different promoters. Such chimeric genes can be transfered into host plants either together in a single expression vector or sequentially using more than one vector.

It is envisioned that the introduction of enhancers or enhancer-like elements into either the native β-ketoacyl-ACP synthetase II promoter or into other promoter constructs will also provide increased levels of primary transcription for antisense RNA or in RNA for β-ketoacyl-ACP synthetase II to accomplish the inventions. This would include viral enhancers such as that found in the 35S promoter (Odell et al., Plant Mol. Biol. (1988) 10:263β272), enhancers from the opine genes (Fromm et al., Plant Cell (1989) 1:977–984), or enhancers from any other source that result in increased transcription when placed into a promoter operably linked to the nucleic acid fragment of the invention.

Of particular importance is the DNA sequence element isolated from the gene for the α-subunit of β-conglycinin that can confer 40-fold seed-specific enhancement to a constitutive promoter (Chen et al., Dev. Genet. (1989) 10:112–122). One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

The invention can also be accomplished by a variety of other methods to obtain the desired end. In one form, the invention is based on modifying plants to produce increased levels of β-ketoacyl-ACP synthetase II by virtue of having significantly larger numbers of copies of the β-ketoacyl-ACP synthetase II gene product. This may result in sufficient increases in β-ketoacyl-ACP synthetase II activity levels to accomplish the invention.

Any 3' non-coding region capable of providing a polyadenylation signal and other regulatory sequences that may be required for the proper expression of the β-ketoacyl-ACP synthetase II coding region can be used to accomplish the invention. This would include the native 3' end of the substantially homologous soybean β-ketoacyl-ACP synthetase II gene(s), the 3' end from a heterologous β-ketoacyl-ACP synthetase II, the 3' end from viral genes such as the 3' end of the 35S or the 19S cauliflower mosaic virus transcripts, the 3' end from the opine synthesis genes, the 3' ends of ribulose 1,5-bisphosphate carboxylase or chlorophyll a/b binding protein, or 3' end sequences from any source such that the sequence employed provides the necessary regulatory information within its nucleic acid sequence to result in the proper expression of the promoter/β-ketoacyl-ACP synthetase II coding region combination to which it is operably linked. There are numerous examples in the art that teach the usefulness of different 3' non-coding regions.

Transformation Methods

Various methods of transforming cells of higher plants according to the present invention are available to those skilled in the art (see EPO Pub. 0 295 959 A2 and 0 318 341 A1). Such methods include those based on transformation vectors based on the Ti and Ri plasmids of Agrobacterium spp. It is particularly preferred to use the binary type of these vectors. Ti-derived vectors transform a wide variety of higher plants, including monocotyledonous and dicotyledonous plants, Sukhapinda et al., Plant Mol. Biol. (1987) 8:209–216; Potrykus, Mol. Gen. Genet. (1985) 199:183). Other transformation methods are available to those skilled in the art, such as direct uptake of foreign DNA constructs (see EPO Pub. 0 295 959 A2), techniques of electropotation (Fromm et al., Nature (1986) (London) 319:791) or high-velocity ballistic bombardment with metal particles coated with the nucleic acid constructs (Kline et al., Nature (1987) (London) 327:70). Once transformed, the cells can be regenerated by those skilled in the art.

Of particular relevance are the recently described methods to transform foreign genes into commercially important crops, such as rapeseed (De Block et al., Plant Physiol. (1989) 91: 694–701), sunflower (Everett et al., Bio/Technology (1987) 5:1201), and soybean (Christou et al., Proc. Natl. Acad. Sci USA (1989) 86:7500–7504.

Application to RFLP Technology

The use of restriction fragment length polymorphism (RFLP) markers in plant breeding has been well-documented in the art (Tanksley et al., Bio/Technology (1989) 7:257–264). The nucleic acid fragment of the invention indicates two gene copies by Southern blotting. Both of these have been mapped on a soybean RFLP map (Tingey et al., J. Cell Biochem. (1990), Supplement 14E p. 291, abstract R153) and can be used as RFLP markers for traits linked to these mapped loci. These traits will include altered levels of palmitic, stearic and oleic acid. The nucleic acid fragment of the invention can also be used to isolate the β-ketoacyl-ACP synthetase II gene from variant (including mutant) soybeans with altered stearic acid levels. Sequencing of these genes will reveal nucleotide differences from the normal gene that cause the variation. Short oligonucleotides designed around these differences may be used as hybridization probes to follow the variation in stearic, palmitic and oleic acids. Oligonucleotides based on differences that are linked to the variation may be used as molecular markers in breeding these variant oil traits.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and nonpatent literature, referred to in this specification are expressly incorporated by reference herein.

EXAMPLE 1

ISOLATION OF cDNA FOR SOYBEAN SEED
β-KETOACYL-ACP SYNTHETASE II
PREPARATION OF PALMITOYL-ACP

Purification of Acyl Carrier Protein (ACP) from *E. coli*

To frozen *E. coli* cell paste, (0.5 kg of 1/2 log phase growth of *E. coli* B grown on minimal media and obtained from Grain Processing Corp, Muscatine, IA) was added 50 mL of a solution 1M in Tris, 1M in glycine, and 0.25 M in EDTA. Ten mL of 1M $MgCl_2$ was added and the suspension was thawed in a water bath at 50° C. As the suspension approached 37° C. it was transferred to a 37° C. bath, made to 10 mM in 2-mercaptoethanol and 20 mg of DNAse and 50 mg of lysozyme were added. The suspension was stirred for 2 h, then sheared by three 20 sec bursts in a Waring Blendor. The volume was adjusted to 1 L and the mixture was centrifuged at 24,000×g for 30 min. The resultant supernatant was centrifuged at 90,000×g for 2 h. The resultant high-speed pellet was saved for extraction of acyl-ACP synthase (see below) and the supernatant was adjusted to pH 6.1 by the addition of acetic acid. The extract was then made to 50% in 2-propanol by the slow addition of cold 2-propanol to the stirred solution at 0° C. The resulting precipitate was allowed to settle for 2 h and then removed by centrifugation at 16,000×g. The resultant supernatant was adjusted to pH 6.8 with KOH and applied at 2 mL/min to a 4.4×12 cm column of DEAE-Sephacel which had been equilibrated in 10 mM MES, pH 6.8. The column was washed with 10 mM MES, pH 6.8 and eluted with 1 L of a gradient of LiCl from 0 to 1.7M in the same buffer. Twenty mL fractions were collected and the location of eluted ACP was determined by applying 10 μL of every second fraction to a lane of a native polyacrylamide (20% acrylamide) gel electrophoresis (PAGE). Fractions eluting at about 0.7M LiCl contained nearly pure ACP and were combined, dialyzed overnight against water and then lyophilized.

Purification of *E. coli* Acyl-ACP Synthase

Membrane pellets resulting from the high-speed centrifugation described above were homogenized in 380 mL of 50 mM Tris-Cl, pH 8.0, and 0.5M in NaCl and then centrifuged at 80,000×g for 90 min. The resultant supernatant was discarded and the pellets resuspended in 50 mM Tris-Cl, pH 8.0, to a protein concentration of 12 mg/mL. The membrane suspension was made to 2% in Triton X-100 and 10 mM in $MgCl_2$, and stirred at 0° C. for 20 min before centrifugation at 80,000×g for 90 min. The protein in the resultant supernatant was diluted to 5 mg/mL with 2% Triton X-100 in 50 mM Tris-Cl, pH 8.0 and then made to 5 mM ATP by the addition of solid ATP (disodium salt) along with an equimolar amount of $NaHCO_3$. The solution was warmed in a 55° C. bath until the internal temperature reached 53° C. and was then maintained at between 53° C. and 55° C. for 5 min. After 5 min the solution was rapidly cooled on ice and centrifuged at 15,000×g for 15 min. The supernatant from the heat-treatment step was loaded directly onto a column of 7 mL Blue Sepharose 4B which had been equilibrated in 50 mM Tris-Cl, pH 8.0, and 2% Triton X-100. The column was washed with 5 volumes of the loading buffer, then 5 volumes of 0.6M NaCl in the same buffer and the activity was eluted with 0.5M KSCN in the same buffer. Active fractions were assayed for the synthesis of acyl-ACP, as described below, combined, and bound to 3 mL settled-volume of hydroxylapatite equilibrated in 50 mM Tris-Cl, pH 8.0, 2% Triton X-100. The hydroxylapatite was collected by centrifugation, washed twice with 20 mL of 50 mM Tris-Cl, pH 8.0, 2% Triton X-100. The activity was eluted with two 5 mL washes of 0.5M potassium phosphate, pH 7.5, 2% Triton X-100. The first wash contained 66% of the activity and it was concentrated with a 30 kD membrane filtration concentrator (Amicon) to 1.5 mL.

Synthesis of Palmitoyl-ACP

A solution of palmitic acid (120 nmol) prepared in methanol was dried in glass reaction vials. The ACP preparation described above (1.15 mL, 32 nmol) was added along with 0.1 mL of 0.1M ATP, 0.05 mL of 80 mM dithiothreitol (DTT), 0.1 mL of 8M LiCl, and 0.2 mL of 3% Triton X-100 in 0.5 M Tris-Cl, pH 8.0, with 0.1M $MgCl_2$. The reaction was mixed thoroughly, 0.3 mL of the acyl-ACP synthase preparation was added and the reactions were incubated at 37° C. After 2 h the reaction mix was diluted 1 to 4 with 20 mM Tris-Cl, pH 8.0, and applied to a 1 mL DEAE-Sephacel column equilibrated in the same buffer. The column was washed in sequence with 5 mL of 20 mM Tris-Cl, pH 8.0, 5 mL of 80% 2-propanol in 20 mM Tris-Cl, pH 8.0, and eluted with 0.5M LiCl in 20 mM Tris-Cl, pH 8.0. The column eluate was passed directly onto a 3 mL column of octyl-sepharose CL-4B which were washed with 10 mL of 20 mM potassium phosphate, pH 6.8, and then eluted with 35% 2-propanol in 2 mM potassium phosphate, pH 6.8. A 2 μL aliquot of the eluted product was lyophilized and redissolved in 2 μL of 0.125M Tris-Cl (pH 6.8), 4% SDS, 20% glycerol and 10% 2-mercapto-ethanol. The product was separated by electrophoresis in a SDS-20% acrylamide gel in a Pharmacia Phast-Gel apparatus. The gel was stained in the same apparatus using Fast Stain (Zoion Research, Inc., Boston, Mass.). The concentration of palmitoyl-ACP was estimated by comparison with known concentrations of *E. coli* ACP, separated in the same gel. The remainder of the eluted product was lyophilized and redissolved in distilled water to a final concentration of 10 μM.

Preparation of Alkyl-ACP Affinity Column

Intial experiments led Applicants to conclude that, unlike acyl-ACP thioesterases and δ-9 desaturases, β-ketoacylsynthetase II did not bind to a hexadecyl-ACP affinity column.

Applicants hypothesized that, since KAS II is somewhat specific for 16-carbon fatty acids, shortening the acyl chain length of the alkyl-ACP column by 2 carbons would be more effective in the purification of KAS II. The tetradecyl-ACP affinity column was therefore synthesized in a manner similar to the hexadecyl-ACP affinity column described by Hitz (WO92/11373) except that N-tetradecyliodoacetamide was substituted for N-hexadecyliodoacetamide.

Synthesis of N-Tetradecyliodoacetamide

1-Tetradecylamine (3.67 mmol) was dissolved in 14 8 mL of $CH_2Cl_2$, cooled to 4° C. and 2 83 μmol of iodoacetic anhydride in 11.3 mL of $CH_2Cl_2$ was added dropwise to the stirred solution. The solution was warmed to room temperature and held for 2 h. The reaction mixture was diluted to about 50 mL with $CH_2Cl_2$ and washed 3 times (25 mL) with saturated sodium bicarbonate solution and then 2 times with water. The volume of the solution was reduced to about 5 mL under vacuum and passed through 25 mL of silica gel-in diethyl ether. The eluate was reduced to an off-white powder under vacuum.

Synthesis of N-Tetradecylacetamido-S-ACP

E. coli ACP prepared as above (10 mg in 2 mL of 50 mM Tris-Cl, pH 7.6) was treated at 37° C. with 50 mM DTT for 2 h. The solution was made to 10% trichloroacetic acid (TCA), held at 0° C. for 20 min and centrifuged to pellet. The resultant pellet was washed (2×2 mL) with 0.1M citrate, pH 4.2 and redissolved in 3 mL of 50 mM potassium phosphate buffer. The pH of the ACP solution was adjusted to 7.5 with 1M KOH and 3 mL of N-tetradecyliodoacetamide (3 mM in 2-propanol) was added. A slight precipitate of the N-tetraadecyliodoacetamide was redissolved by warming the reaction mix to 45° C. The mixture was held at 45° C. for 6 h. SDS-PAGE on 20% acrylamide gel showed approximately 80% conversion to an ACP species of intermediate mobility between the starting, reduced ACP and authentic palmitoyl-ACP. Excess N-tetradecyliodoacetamide was removed from the reaction mix by 4 extractions (3 mL) with $CH_2Cl_2$ with gentle mixing to avoid precipitation of the protein at the interface.

Coupling of N-Tetradecylacetamido-S-ACP to CNBr-activated Sepharose 4B

Cyanogen bromide-activated Sepharose 4B (Pharmacia, 2 g) was suspended in 1 mM HCl and extensively washed by filtration and resuspension in 1 mM HCl and finally one wash in 0.1M $NaHCO_3$, pH 8.3. The N-tetradecylacetamido-S-ACP prepared above was diluted with an equal volume of 0.2M $NaHCO_3$, pH 8.3. The filtered cyanogen bromide-activated Sepharose 4B (about 5 mL) was added to the N-tetradecylacetamido-S-ACP solution, the mixture was made to a volume of 10 mL with the 0.1M $NaHCO_3$, pH 8.3, and mixed by tumbling at room temperature for 6 h. Protein remaining in solution (Bradford assay) indicated approximately 85% binding. The gel suspension was collected by centrifugation, washed once with the 0.1M $NaHCO_3$, pH 8.3, and resuspended in 0.1M ethanolamine adjusted to pH 8.5 with HCl. The suspension was allowed to stand at 4° C. overnight and then washed by centrifugation and re-suspension in 12 mL of 0.1M acetate, pH 4.0, 0.5M in NaCl and then 0.1M $NaHCO_3$, pH 8.3, 0.5M in NaCl. The alkyl-ACP Sepharose 4B was packed into a 1×5.5 cm column and washed extensively with 20 mM bis-tris propane-Cl (BTP-Cl), pH 7.2, before use.

Preparation of Malonyl Transacylase

E. coli malonyl transacylase was prepared according to the method of Greenspan et al. (J. Biol. Chem. (1969) 244:6477–6485) and treated by the method of Garwin et al. (J. Biol. Chem. (1980) 255:11949–11956) to inactivate residual acyl synthase activities.

β-Ketoacyl-ACP Synthetase II Assay

β-ketoacyl-ACP synthetase II was assayed as described by Garwin et al. (J. Biol. Chem. (1980) 55:11949–11956). A buffer solution of 600 mM Tris-Cl (pH 7.0), 4 mg/mL BSA, 4 mM EDTA and 4 mM DTT containing 10 mM ACP and malonyl transacylase (ca. 1 mU) in a final volume of 7.35 μL was incubated at 37° C. for 10 min, to allow the chemical reduction of the ACP and malonyl transacylase. To the reaction was added [2-$^{14}$C] malonyl-CoA (50 Ci/mol) at a final concentration of 10 μM and palmitoyl-ACP at final concentration of 1 μM. The reaction was started by the addition of 15 μL of soybean seed extract containing β-ketoacyl-ACP synthetase II activity and incubated at 37° C. for 10 min. The final reaction volume was 30 μL, containing a final buffer concentration of 1 mM EDTA, 150 mM Tris-Cl (pH 7.0), 1 mg/mL BSA and 1 mM DTT.

Reactions were terminated by the addition of 400 μL of a solution of reducing agent containing 30% tetrahydrofuran, 0.4M KCl and 5 mg/mL sodium borohydride in 0.1M $K_2HPO_4$. The mixture was incubated at 30° C. for 30 min. Toluene (400 μL) was added and the contents of the tube well mixed. A 400 μL aliquot of the upper phase was mixed with 5 mL of ScintiVerse Bio HP (Fisher) scintillation fluid and radioactivity of the reduced product was determined by scintilation counting.

Purification of Soybeam β-Ketoacyl-ACP Synthetase II

Developing soybean seeds, ca. 20–25 days after flowering, were harvested and stored at −80° C. until use. One kg of the seeds was added while frozen to 2-L of a buffer consisting of 50 mM Tris/HCl pH 8.0, 2 mM DTT and 0.2 mM EDTA in a Waring blendor and ground until thawed and homogenized. The homogenate was centrifuged at 14,000×g for 20 min, decanted and the supernatant was centrifuged at 35,000× g for 45 min. The resulting high-speed supernatant was adjusted to 55% saturation with ammonium sulfate at 4° C. and protein was allowed to precipitate for 30 min before centrifugation at 14,000× g for 15 min to remove precipitated proteins. The supernatant was adjusted to 75% saturation of ammonium sulfate and incubated at 4° C. for a further 30 min. The precipitated proteins were collected by centrifugation at 14,000× g for 15 min. The precipitate was dissolved in 20 mM $K_2HPO_4/KH_2PO_4$ buffer, pH 7.2 containing 1 mM DTT and dialyzed overnight against 15 L of the same buffer at 5 mM. The dialyzed ammonium sulfate fraction was adjusted to a buffer concentration of 20 mM and a protein concentration of 5 mg/mL. The resulting solution was applied to a 200 mL column of hydroxylapatite. The flow rate was 3 mL/min and the column was washed with the application buffer until the absorbance at 280 nm monitored at the column efflux returned to zero after application of the protein. β-ketoacyl-ACP synthetase II activity was eluted with a gradient of 20 mM to 1000 mM of the same buffer and 9 mL fractions were collected. β-Ketoacyl-ACP synthetase II activity eluted at a phosphate concentration between 72 and 77 mM.

The combined hydroxylapatite fractions were dialyzed overnight against 4 L of 10 mM BTP-Cl buffer, pH 7.2 with 1 mM DTT. The dialysate was centrifuged at 22,000× g for 20 min and the supernatant was applied at a flow rate of 2 mL/min to Mono Q HR 16/10 anion exchange column (Pharmacia) equilibrated in the same buffer. After application of the protein, the column was washed with the same buffer until the absorbance at 280 nm monitored at the column efflux returned to near zero. β-Ketoacyl-ACP synthetase II was eluted with a linear gradient of 0 mM to 500 mM NaCl in the same BTP-Cl buffer. The β-ketoacyl-ACP synthetase II activity eluted from an NaCl concentration of 0.150M to 0.169M. Active fractions were desalted on Bio-Rad 10DG desalting columns and then combined before application to the alkyl-ACP affinity column. The column was loaded at 1 mL/min, then washed with 10 mM BTP-Cl, pH 7.2, until the absorbance at 280 nm monitored at the column efflux returned to zero. The column was then washed with 0.1M NaCl in the same buffer until a protein peak was washed from the column and the column efflux 280 nm absorbance returned to zero before elution of the β-ketoacyl-ACP synthetase II activity with 0.8M NaCl in the BTP-Cl buffer system.

The eluant from the alkyl-ACP column was concentrated in an Amicon Centricon 30 to a final volume of approximately 50 μL. The volume of the concentrate was adjusted to 500 μL with 0.1M potassium phosphate buffer, pH 7.2, and applied at a flow rate of 1.0 mL/min to an UltraPac TSK-G3000SW HPLC gel filtration column (0.75×60 cm, Pharmacia) which was equlibrated with 0.1M potassium phosphate buffer at pH 7.2. The column was calibrated with Blue dextran and Pharmacia molecular weight standards (25 to 440 kD) and showed a linear relationship (r=0.95) between $K_{av}$ and the $\log_{10}$ of the molecular weight of the eluted protein over the protein molecular weight range 30 to 400 kD. β-Ketoacyl-ACP synthetase II activity eluted at 17 min after application, corresponding to a $K_{av}$ of 0.07 and an approximate molecular weight of 100 kD.

β-Ketoacyl-ACP synthetase II containing fractions from the gel filtration column contained from up to 100 μg of protein, depending upon the preparation, and were enriched in specific activity of the β-ketoacyl-ACP synthetase II by approximately 20,000 fold over the total cell extracts.

When analyzed by SDS-polyacrylmide gel electrophoresis, the fractions from the gel filtration column containing β-ketoacyl-ACP synthetase II activity contained a single polypeptide with an estimated molecular weight of 55 kD.

Preparation of Antibodies Against Soybean Seed β-Ketoacyl-ACP Synthetase II

β-Ketoacyl-ACP synthetase II purified through the alkyl-ACP affinity step was denatured with DTT and SDS, applied to a gradient polyacrylamide gel (9 to 15% acrylamide), and subjected to SDS electrophoresis. The developed gel was stained with a 9:1 mixture of 0.1% Coomassie blue in 50% methanol:0.5% Serva blue in 50% methanol then partially destained with 3% glycerol in 20% methanol. The peptide at 55 kD was cut from the gel, frozen in liquid nitrogen, then ground to a powder and suspended in 50 mM sodium phosphate buffer. The suspended gel with protein was sent for antibody production in New Zealand White rabbit by Hazelton Research Products Inc., Denver, Pa. Serum obtained after three injections was precipitated by the addition of 50% ammonium sulfate at 4° C. and incubation for 30 min. The precipitated proteins were collected by centrifugation at 14,000×g for 15 min. The precipitate was dissolved in 10 mM Tris-Cl buffer, pH 8.5 and dialyzed overnight against 15 L of the same buffer at 5 mM. The dialyzed ammonium sulfate fraction was adjusted to a buffer concentration of 10 mM and a protein concentration of 10 mg/mL. The resulting solution was applied to a 200 mL DEAE ion-exchange column at a flow rate of 3 mL/min. Antibodies were eluted with a linear gradient from 0 to 0.6M NaCl and IgG subclass elution was monitored by gel electrophoresis. The IgG fractions were desalted and concentrated (Amicon Centricon 30) and adjusted to a final buffer concentration of 10 mM Tris-Cl, pH 8.5, in a volume of 3 mL. Purified antibodies of the 55 kD peptide identified that peptide in Western analysis, but also cross-reacted with two other peptides at 75 kD and >100 kD which were not included in the antigen preparations.

N-Terminal Amino Acid Sequence from the β-Ketoacyl-ACP synthetase II

β-Ketoacyl-ACP synthetase II purified through the alkyl-ACP affinity step of the standard scheme was denatured with DTT and SDS, applied to a homogenous polyacrylamide gel (12% acrylamide), and subjected to SDS electrophoresis. Proteins in the developed gel were electrophoretically transferred to a PVDF membrane (Millipore Immobilon-P) and the membrane was stained with 0.1% Coomassie in 50% methanol. The 55 kD band was excised from the membrane and used to determine the N-terminal amino acid sequence on an Applied Biosystems 470A Gas Phase Sequencer. PTH amino acids were analyzed on an Applied Biosystems 120 PTH amino Acid. Analyzer. The N-terminal sequence was determined to be: V-I-L-K-N-L-K-L-X-Y-S (SEQ ID NO:2)

Cloning of Soybean Seed β-Ketoacyl-ACP Synthetase II cDNA

Based on the N-terminal sequence from cycle 1 through 8 of the N-terminal sequence, a set of 192 degenerate 22 nucleotide long probes were designed for use as a hybridization probe:

| PROTEIN SEQUENCE: | V | I | L | K | N | L | K | L | (Amino acids 1–8 of (SEQ ID NO:2) |
|---|---|---|---|---|---|---|---|---|---|
| DNA SEQUENCE: | 5'-GTN | ATT<br>C<br>A | TTG<br>A<br>CTN | AAG<br>A | AAC | TTG<br>A<br>CTN | AAG | T | (SEQ ID NO:3) |
| PROBE: (A) | 5'-GTI | ATC<br>A<br>T | CTC<br>T | AAA<br>G | AAC<br>T T | CTI | AAA<br>G | T | (SEQ ID NO:4) |
| (B) | 5'-GTI | ATC | TTA | AAA | AAC | CTI | AAA | T | (SEQ ID NO:5) |

|   | A |   | G |   | G |   | T | T |   | G |
|---|---|---|---|---|---|---|---|---|---|---|
|   | T |   |   |   |   |   |   |   |   |   |

The design took into account the codon bias in representative soybean seed genes encoding Bowman-Birk protease inhibitor (Hammond et al., J. Biol. Chem. (1984) 259:9883–9890), glycinin subunit A-2B-1a (Utsumi et al., Agric. Biol. Chem. (1987) 51:3267–3273), lectin (le-1) (Vodkin et al., Cell (1983) 34:1023–1031), and lipoxygenase-1 (Shibata et al., J. Biol. Chem. (1987) 262:10080–10085). Four deoxyinosines were used at selected positions of ambiguity.

A cDNA library was made as follows: Soybean embryos (ca. 50 mg fresh weight each) were removed from the pods and frozen in liquid nitrogen. The frozen embryos were ground to a fine powder in the presence of liquid nitrogen and then extracted by Polytron homogenization and fractionated to enrich for total RNA by the method of Chirgwin et al. (Biochemistry (1979) 18:5294–5299). The nucleic acid fraction was enriched for poly $A^+$RNA by passing total RNA through an oligo-dT cellulose column and eluting the poly $A^+$RNA by salt as described by Goodman et al. (Meth. Enzymol. (1979) 68:75–90). cDNA was synthesized from the purified poly $A^+$RNA using cDNA Synthesis System (Bethesda Research Laboratory) and the manufacturer's instructions. The resultant double-stranded DNA was methylated by DNA methylase (Promega) prior to filling-in its ends with T4 DNA polymerase (Bethesda Research Laboratory) and blunt-end ligating to phosphorylated Eco RI linkers using T4 DNA ligase (Pharmacia). The double-stranded DNA was digested with Eco RI enzyme, separated from excess linkers by passing through a gel filtration column (Sepharose CL-4B), and ligated to lambda ZAP vector (Stratagene) according to manufacturer's instructions. Ligated DNA was packaged into phage using Gigapack packaging extract (Stratagene) according to manufacturer's instructions. The resultant cDNA library was amplified as per Stratagene's instructions and stored at –80° C.

Following the instructions in the Lambda ZAP Cloning Kit Manual (Stratagene), the cDNA phage library was used to infect E. coli BB4 cells and plated to yield ca. 35,000 plaques per petri plate (150 mm diameter). Duplicate lifts of the plates were made onto nitrocellulose filters (Schleicher & Schuell). Duplicate lifts from five plates were prehybridized in 25 mL of Hybridization buffer consisting of 6× SSC (0.9M NaCl, 0.09M sodium citrate, pH 7.0), 5× Denhardt's [0.5 g Ficoll (Type 400, Pharmacia), 0.5 g polyvinylpyrrolidone, 0.5 g bovine serum albumin (Fraction V; Sigma)], 1 mM EDTA, 1% SDS, and 100 mg/mL denatured salmon sperm DNA (Sigma Chemical Co.) at 45° C. for 10 h. Fifty pmol of the hybridization probe (see above) were end-labeled in a 52.5 mL reaction mixture containing 50 mM Tris-Cl, pH 7.5, 10 mM $MgCl_2$, 0.1 mM spermidine-HCl (pH 7.0), 1 mM EDTA (pH 7.0), 5 mM DDT, 200 mCi (66.7 pmol) of gamma-labeled $AT^{32}P$ (New England Nuclear) and 25 units of T4 polynucleotide kinase (New England Biolabs). After incubation at 37° C. for 45 min, the reaction was terminated by heating at 68° C. for 10 min. Labeled probe was separated from unincorporated $AT^{32}P$ by passing the reaction through a Quick-Spin™ (G-25 Sephadex®) column (Boehringer Mannhiem Biochemicals). The purified labeled probe ($1.2 \times 10^7$ dpm/pmol) was added to the prehybridized filters, following transfer of the fillers to 10 mL of fresh Hybridization buffer. Following incubation of the filters in the presence of the probe for 48 h in a shaker at 48° C., the filters were washed in 200 mL of Wash buffer (6× SSC, 0.1% SDS) five times for 5 min each at room temperature, then at 48° C. for 5 min and finally at 62° C. for 5 min. The washed filters were air dried and subjected to autoradiography on Kodak XAR-2 film in the presence of intensifying screens (Lightening Plus, DuPont Cronex®) at –80° C. overnight. Six positively-hybridizing plaques were subjected to plaque purification as described in Sambrook et al. (Molecular Cloning, A Laboratory Manual, 2nd ed. (1989), Cold Spring Harbor Laboratory Press).

Following the Lambda ZAP Cloning Kit Instruction Manual (Stratagene), sequences of the pBluescript vector, including the cDNA inserts, from four of six purified phages were excised in the presence of a helper phage and the resultant phagemids were used to infect E. coli XL-1 Blue cells resulting in double-stranded plasmids, pC8, pC12, pC14, pC15, pC16 and pC17. Purity of the clones was checked by colony hybridization and a single, positive colony from each was used for culture preparation.

DNA from the plasmids was made by the alkaline lysis miniprep procedure described in Sambrook et al. (Molecular Cloning, A Laboratory Manual, 2nd ed. (1989) Cold Spring Harbor Laboratory Press). The alkali-denatured double-stranded DNA from pC16 was sequenced using Sequenase® T7 DNA polymerase (US Biochemical Corp.) and the manufacturer's instructions. The sequence of the cDNA insert in plasmid pC16 is shown in SEQ ID NO:1, bases 554 to 2675.

The cDNA insert in plasmid pC16 was removed by digestion with Eco RI and purified by electrophoretic separation on 6% polyacrylamide. The 2.1 kB fragment was localized by ethidium bromide staining, eluted from the gel and precipitated from 0.3M sodium acetate with 50% ethanol. Fifty ng of the resulting DNA fragment was used as the template in a random primer labeling reaction using a labeling kit from Bethesda Research Laboratories. The early development soybean seed cDNA library described above was re-plated at a plaque density of 35,000 per plate and duplicate nitrocellulose lifts from four plates were screened. The prehybridization and hybridization buffer was that described above but the probe annealing conditions were 50° for 40 h. The filter lifts were washed 3 times at room temperature with 0.6× SSC containing 0.1% SDS, then once at 50° C. for 5 min in the same solution. Two additional washes were given for 5 min each at 50° C. in 0.2× SSC, 0.1% SDS followed by a 1 min rinse under the same conditions.

After autoradiography for 20 h, 6 hybridizing plaques were identified. These were plaque purified and excised into Bluescript plasmids as described above. Only one of these, pC16i with a 2.6 kB insert, had an insert size substantially larger than pC16. The alkali-denatured double-stranded DNA from pC16i was sequenced as described above. The sequence of the cDNA insert in plasmid pC16i was 100% homologous with bases 554 through 2675 of the insert in pC16. There was an additional 553 bases at the 5' end of pC16i. The sequence of pC16i is shown in SEQ ID NO:1, bases 1 to 2675.

Use of DC16 as a Probe for Genes from Other Species

Genomic DNA from Arabidopsis thaliana, oilseed rape, soybean, tomato, cotton and tobacco was digested with Bam HI. The digested genomic fragments were separated on an agarose gel and transferred to a nylon membrane as described in Sambrook et al. (Molecular Cloning, A Laboratory Manual, 2nd ed. (1989), Cold Spring Harbor Laboratory Press). The DNA on the membrane was probed with pC16, labeled with ATP-P$^{32}$ by random primer labeling as described above in this example. Genes corresponding to pC16 were identified in all of the above species. This confirms that pC16 will be a useful probe for isolating β-ketoacyl-ACP synthethase II genes from other species.

EXAMPLE 2

EXPRESSION OF SOYBEAN SEED β-KETOACYL-ACP SYNTHETASE II IN *E. COLI*

Construction of Glutathione-S-Transferase-β-Ketoacyl-ACP Synthetase II Fusion Protein Sequences which are inserted into the pGEX-2T plasmid (Pharmacia) directionally correct and in-frame with the start methionine of the interrupted glutathione-s-transferase gene borne on the plasmid are capable of being expressed as fusion proteins consisting of 26 kD of the N-terminal of glutathione-s-transferase plus the amino acids encoded by the inserted sequence (Smith et al., Gene (1988) 67:31–40). Sequencing of pC16i revealed that the cDNA insert of that plasmid was directionaly correct but 1 base out of frame. Two μg of pC16i was digested for 2 h with 30 units of Not I and 30 units of Sal I. These enzymes each cleave once in the polylinker site of the Bluescript plasmid, one each side of the Eco RI cloning site. The reaction was then heated to 75° C. for 15 min. Five units of DNA polymerase I large subunit (New England Biolabs) and 4 μL of a 1 mM equimolar mix of dATP, dCTP, dTTP and dGTP were added and the mixture was incubated at 30° C. and then heated to 75° C. for 15 min. The complete digestion gave two fragments, one of about 3.0 kB which is the linearized Bluescript plasmid and the 2.1 kB cDNA insert. The 2.1 kB fragment was purified by electrophoretic separation on a 1.0% agarose gel run in Tris/borate/EDTA buffer. The fragment was visualized by ethidium bromide staining, cut from the gel, precipitated by the addition of sodium acetate to 0.3M and ethanol to 50%. The pGEX-2T plasmid was digested for 1 h with 50 units of Sma I and then heated to 75° C. for 15 min. One unit of calf intestinal phosphatase (Boehringer Mannheim GmbH) was added to the mix, along with 1 μL of the manufacturers' supplied buffer, and the reaction incubated at 37° C. for 1 h. The reaction was heated to 75° C. for 15 min and then treated with DNA polymerase I and gel purified as described above for the pC16 insert. The purified 2.1 kB pC16 fragment and the pGEX-2T were ligated together by incubation of 100 ng of the fragment and 120 ng of the cut pGEX-2T plasmid in a 25 μL reaction with 10 units of T4 DNA ligase overnight at 16° C. Competent *E. coli* XL-1 blue cells (Statagene) were transformed with 30 ng of the ligated plasmid. Transformants were picked as ampicillin-resistant cells after overnight growth. Six colonies were chosen and mini-preparations of plasmid DNA were made by the alkaline lysis procedure described above. Agarose gel electrophoresis of the six plasmids, cut with Bam HI and Eco RI, next to supercoiled weight standards showed that three of the six pGEX-2T plasmids contained a 2.1 kB insert. One of the three transformed cell lines containing plasmid designated pC16N5 along with a transformed XL-1 line carrying unmodified pGEX-2T were grown for 8 h in 5 mL of LB-ampicilin media. These 5 mL were used to innoculate 200 mL of LB-ampicilin and grown overnight. The overnight cultures were diluted 1:1 into fresh LB-ampicilin media which also contained 10 mM isopropyl thiogalactoside and growth was continued for 2.5 h at 37° C. Cells were harvested by centrifugation and re-suspended in 12 mL of phosphate-buffered saline and recentrifuged at 400× g for 10 min. The pellet was resuspended in 4 mL of phosphate-buffered saline containing 1 mg/mL each of pepstatin and leupeptin and 1 μL/mL of each of the following: 1M DTT, 100 mM phenylmethylsulfonyl fluoride (PMSF) and 10.0 mM sodium metabisulfite. The suspension was sonicated (2×5 sec), centrifuged at 12,000×g for 10 min and the supernatant mixed for 30 min at 4° C. with a 50% suspension of glutathione-Sepharose 4B in phosphate-buffered saline (PBS). The mixture was then poured into a 25 mL column and washed first with 100 mL of phosphate-buffered saline and-then with 100 mL of 50 mM Tris-Cl, pH 8.0. Glutathione-S-transferase/pC16N5 protein was eluted from the glutathione-Sepharose with 5 mM reduced glutathione. A subsample containing 10 μg protein was taken and added to 20 μL of SDS sample buffer for analysis by SDS-PAGE and Western blotting. The remaining sample was used for making rabbit antibodies as described for the β-ketoacyl-ACP synthetase II in Example 1. The pC16N5/glutathione-S-transferase fusion protein reacted specifically with the β-ketoacyl-ACP synthetase II antibodies described in Example 1. The immunoreactive band had a molecular weight of 80 kD which corresponds to the 26 kD glutathione-S-transferase and a 54 kD fusion protein. There was a second immunoreactive band at 54 kD which was deduced to be the fusion protein without the 26 kD glutathione-S-transferase attached to its N-terminus. Neither the 54 kD nor the 80 kD protein reacted with antibodies prepared against soybean β-ketoacyl-ACP synthetase I. The pC16N5 fusion protein preparation did not have any β-ketoacyl-ACP synthetase II activity.

The antibodies prepared against the pC16N5/glutathione-S-transferase fusion protein (a 5 mL test bleed four weeks after initial innoculation) identified a protein of about 55 kD in Western blots of soybean cell extracts. Aliquots (100 μL) of a 50% ammonium sulfate supernatant of soybean extracts, made from 5 g of immature soybean seeds prepared as described in Example 1, were incubated for 1 h with dilutions of the pC16N5 antibody or preimmune serum, in a final volume of 200 μL. This was followed by incubation for 30 min with 20 μL of insoluble protein A (Sigma Chemical Co). The mixture was then centrifuged at 10,000×g for 5 min and a 15 μL aliquot of the supernatant assayed for β-ketoacyl-ACP synthetase II activity as described in Example 1. The results are shown in Table 2 below:

TABLE 2

| Dilution (Serum:PBS) | PreImmune Serum (β-ketoacyl-ACP synthetase II activity) (cpm/assay) | PostImmune Serum |
| --- | --- | --- |
| 1:100 | 766 | 750 |
| 1:10 | 710 | 614 |
| 1:2 | 580 | 508 |
| 1:1 | 580 | 384 |

β-ketoacyl-ACP synthetase II activity is inhibited by 50% when incubated with a 1:1 dilution of pC16N5 antibody and 25% when incubated with preimmune sera at the same dilution.

EXAMPLE 3

USE OF SOYBEAN SEED β-KETOACYL-ACP SYNTHETASE II SEQUENCE IN PLASMID AS A RESTRICTION FRAGMENT LENGTH POLYMORPHISM (RFLP) MARKER

The cDNA insert from plasmid pC16 was removed from the Bluescript vector by digestion with restriction enzyme Eco RI in standard conditions as described in Sambrook et al. (Molecular Cloning, A Laboratory Manual, 2nd ed. (1989) Cold Spring Harbor Laboratory Press) and labeled with 32p using a Random Priming Kit from Bethesda Research Laboratories under conditions recommended by the manufacturer. The resulting radioactive probe was used to probe a Southern blot (Sambrook et al., Molecular Cloning, A Laboratory Manual, 2nd ed. (1989) Cold Spring Harbor Laboratory Press) containing genomic DNA from soybean [*Glycine max* (cultivar Bonus) and *Glycine soja* (PI81762)], digested with one of several restriction enzymes. After hybridization and washes under standard conditions (Sambrook et al. Molecular Cloning, A Laboratory Manual, 2nd ed. (1989), Cold Spring Harbor Laboratory Press), autoradiograms were obtained and different patterns of hybridization (polymorphisms) were identified in digests performed with restriction enzymes Bam HI, Eco RV and Eco RI. The same probe was then used to map the polymorphic pC16 loci on the soybean genome, essentially as described by Helentjaris et al. (Theor. Appl. Genet. (1986) 72:761–769). Plasmid pC16 probe was applied, as described above, to Southern blots of EcoRI, PstI, EcoRV, BamHI, or HindIII digested genomic DNAs isolated from 68 F2 progeny plants resulting from a *G. max* Bonus× *G. soja* PI81762 cross. The bands on the autoradiograms were interpreted as resulting from the inheritance of either paternal (Bonus) or maternal (PI81762) pattern, or both (a heterozygote). The resulting data were subjected to genetic analysis using the computer program Mapmaker (Lander et al., Genomics (1987) 1:174–181). In conjunction with previously obtained data for 436 anonymous RFLP markers in soybean (Tingey et al., J. Cell. Biochem., Supplement 14E (1990) p. 291, abstract R153], Applicants were able to position two different genetic loci corresponding to the pC16 probe on the soybean genetic map. This confirms that there are at least two separate genes, located on different chromosomes, for β-ketoacyl-ACP synthetase II in the soybean genome. This information will be useful in soybean breeding targeted towards developing lines with altered saturate levels.

Plasmid pC16 was also used to probe Southern blots of Eco RI or Bam HI digested genomic DNAs isolated from 209 progeny plants resulting from a cross between *G. soja* PI440913b and G. max HO2, a variant line with altered levels of fatty acids. In conjunction with data for 127 previously mapped RFLP markers, applicants were able to use the pC16 probe to-correlate genotype at one of the pC16 loci with variation for stearic acid content segregating in the cross of HO2×PI440913b. This confirms the utility of the probe for the selection of individual soybean lines with altered stearic acid content.

EXAMPLE 4

Construction of a Vector for Transformation of Tobacco and *Brassica napus* for Increased expression of β-ketoacylsynthetase II in Developing Seeds Detailed procedures for manipulation of DNA fragments by restriction endonuclease digestion, size separation by agarose gel electrophoresis, isolation of DNA fragments from agarose gels, ligation of DNA fragments, modification of cut ends of DNA fragments and transformation of *E. coli* cells with circular DNA plasmids are all described in Sambrook et al., (Molecular Cloning, A Laboratory Manual, 2nd ed (1989) Cold Spring Harbor Laboratory Press, Ausubel et al., Current Protocols in Molecular Biology (1989) John Wiley & Sons) which are incorporated in their entirety herein.

The soybean β-ketoacylsynthetase II cDNA was modified at its 5' end by adding a unique Sma I site just upstream of the start methionine. This was done by PCR amplification of bases 173–535 of the 5' end of the β-ketoacylsynthetase II cDNA (SEQ ID NO:1). The sense PCR primer was an oligonucleotide (MBM 44) containing bases 173–194 of SEQ ID NO:1 with an additional three bases, CGG, added between base 180 and base 181 to create the Sma I site without changing the reading frame of the cDNA. The antisense primer was an oligonucleotide (MBM 45) which was the exact complement of bases 511 to 535 of SEQ ID NO:1, which includes a unique Eco RI site. The template for the PCR reaction was 1 ng of plasmid pC16, described in Example 1 above, linearized with Sma I and gel purified. The 365 bp fragment was amplified in the presence of 50 ng of each primer, MBM 44 and MBM 45, for 20 cycles of 94° C./1 min, 50° C./1 min and 73° C./2 min in a Perkin-Elmer thermocycler using a GeneAmp kit (Perkin-Elmer-Cetus) and other reaction conditions as recommended by the manufacturer. The 365 bp fragment was gel purified and cut with Sma I and Eco RI. The Sma I/Eco RI fragment was ligated to the 1804 bp β-ketoacylsynthetase II cDNA fragment excised from pC16 with Eco RI and Kpn I and the 2154 bp product was ligated into the Sma I/Kpn I site of pBluescript. The modified β-ketoacylsynthetase II cDNA was sequenced, as described in Example 1, through the 5' region with the pBluescript −20M13 primer (Stratagene) and with an antisense primer which was the exact complement of bases 621 through 641 of SEQ ID NO:1. The resulting DNA sequence showed that the 2154 bp PCR/ligation product contained a 5' DNA sequence corresponding exactly to bases 173–535 of SEQ ID NO:1 except for the intended changes described above. The modified soybean β-ketoacylsynthetase II was excised from pBluescript with Sma I and Asp 718 and the resulting 2160 bp was filled in at the Asp 718 end with Klenow. This fragment is referred to below as the "modified 2.2 kb cDNA encoding the soybean β-ketoacylsynthetase II".

Sequences of the modified 2.2 kb cDNA encoding the soybean β-ketoacylsynthetase II were placed in the sense orientation behind the promoter region from the a' subunit of the soybean storage protein β-conglycinin to provide embryo specific expression and high expression levels.

An embryo specific expression cassette has been constructed to serve as the basis for chimeric gene constructs for sense expression of messenger RNA from the cDNA's encoding the β-ketoacylsynthase II. The vector pCW109 was produced by the insertion of 555 base pairs of the β-conglycinin (a' subunit of the 7s seed storage protein) promoter from soybean (Glycine max), the β-conglycinin 5' untranslated region followed by a multiple cloning sequence containing the restriction endonuclease sites for Nco I, Sma I, Kpn I and Xba I, then 1174 base pairs of the common bean phaseolin 3' untranslated region into the Hind III site in the cloning vector pUC18 (BRL). The μ-conglycinin promoter sequence represents an allele of the published β-conglycinin gene (Doyle et al. (1986) J. Biol. Chem. 261:9228–9238) due to differences at 27 nucleotide positions. Further sequence description may be found in Slightom (W091/13993). The sequence of the 3' untranslated region of phaseolin is described in (Slightom et al., (1983) Proc. Natl. Acad. Sci. USA, 80:1897–1901).

To facilitate use in sense constructions, the Nco I site and potential translation start site in the plasmid pCW109 was destroyed by digestion with Nco I, mung bean exonuclease digestion and re-ligation of the blunt site to give the modified plasmid pM109A.

The β-conglycinin promoter:phaseolin 3' end was released from the modified pM109A by Hind III digestion, filled in by reaction with Klenow, isolated and ligated into the Sma I site of pUC19 (Stratagene) to give the modified plasmid pCBT. The modified 2.2 kb cDNA encoding the soybean β-ketoacylsynthetase II was ligated into the Sma I site of pCBT to yield the plasmid pCSKS II. The sense orientation of the insert was checked by digestion of pCSKS II with Eco RI (vectors with a sense KAS II yield a 0.9 kb fragment). The vector for transformation of plants using *Agrobacterium tumefaciens* with the sense constructions of β-ketoacylsynthase II under control of the β-conglycinin promoter for introduction into plants was produced by constructing a binary Ti plasmid vector system (Brevan, (1984) Nucl. Acids Res. 12:8711–8720). The vector for this system, (pZS199) is based on a vector which contains: (1) the chimeric gene nopaline synthase/neomycin phosphotransferase as a selectable marker for transformed plant cells (Brevan et al. (1984) Nature 304: 184–186); (2) the left and right borders of the T-DNA of the Ti plasmid (Brevan et al. (1984) Nucl. Acids Res. 12:8711–8720); (3) the *E. coli* lacZ a-complementing segment (Vieria and Messing (1982) Gene 19:259–267) with unique restriction endonuclease sites for Eco RI, Kpn I, Bam HI and Sal I; (4) the bacterial replication origin from the Pseudomonas plasmid pVS1 (Itoh et al. (1984) Plasmid 1:206–220); and (5) the bacterial neomycin phosphotransferase gene from Tn5 (Berg et al. (1975) Proc. Natnl. Acad. Sci. U.S.A. 72:36.28–3632) as a selectable marker for transformed *A. tumefaciens*. The nopaline synthase promoter in the plant selectable marker was replaced by the 35S promoter (Odell et al. (1985) Nature, 313:810–813) by a standard restriction endonuclease digestion and ligation strategy. The 35S promoter is required for efficient *Brassica napus* and tobacco transformation as described below.

Transcriptional units of the type [β-conglycinin promoter:sense β-ketoacylsynthetase II:phaseolin 3' end] were isolated from pCBT by digestion with both Kpn I and Sal I. This allowed for the directional insertion of the transcriptional unit into the cloning region of pZS199 to give a transformation vector, pZCSKS II, in which the orientation of the translational unit of the selectable marker gene was the same as that of the introduced gene.

EXAMPLE 5

Agrobacterium Mediated Transformation of *Brassica napus*

The binary vector, pZCSKS II, constructed by insertion of embryo specific promoters driving the sense expression of β-ketoacylsynthetase II into pZS199 was transferred by a freeze/thaw method (Holsters et al. (1978) Mol Gen Genet 163: 181–187) to the Agrobacterium strain LBA4404/pAL4404 (Hockema et al. (1983), Nature 303:179–180).

*Brassica napus* cultivar "Westar" was transformed by co-cultivation of seedling pieces with disarmed *Agrobacterium tumefaciens* strain LBA4404 carrying the the appropriate binary vector.

*B. napus* seeds were sterilized by stirring in 10% Chlorox, 0.1% SDS for thirty min, and then rinsed thoroughly with sterile distilled water. The seeds were germinated on sterile medium containing 30 mM $CaCl_2$ and 1.5% agar, and grown for six days in the dark at 24° C.

Liquid cultures of Agrobacterium for plant transformation were grown overnight at 28° C. in Minimal A medium containing 100 mg/L kanamycin. The bacterial cells were pelleted by centrifugation and resuspended at a concentration of 108 cells/mL in liquid Murashige and Skoog Minimal Organic medium containing 100 μM acetosyringone.

*B. napus* seedling hypocotyls were cut into 5 mm segments which were immediately placed into the bacterial suspension. After 30 min, the hypocotyl pieces were removed from the bacterial suspension and placed onto BC-28 callus medium containing 100 μM acetosyringone. The plant tissue and Agrobacteria were co-cultivated for three days at 24° C. in dim light.

The co-cultivation was terminated by transferring the hypocotyl pieces to BC-28 callus medium containing 200 mg/L carbenicillin to kill the Agrobacteria, and 25 mg/L kanamycin to select for transformed plant cell growth. The seedling pieces were incubated on this medium for three weeks at 24° C. under continuous light.

After three weeks, the segments were transferred to BS-48 regeneration medium containing 200 mg/L carbenicillin and 25 mg/L kanamycin. Plant tissue was subcultured every two weeks onto fresh selective regeneration medium, under the same culture conditions described for the callus medium. Putatively transformed calli grow rapidly on regeneration medium; as calli reached a diameter of about 2 mm, they were removed from the hypocotyl pieces and placed on the same medium lacking kanamycin Shoots began to appear within several weeks after transfer to BS-48 regeneration medium. As soon as the shoots formed discernable stems, they were excised from the calli, transferred to MSV-1A elongation medium, and moved to a 16:8-hour photoperiod at 24° C.

Once shoots had elongated several internodes, they were cut above the agar surface and the cut ends were dipped in Rootone. Treated shoots were planted directly into wet Metro-Mix 350 soiless potting medium. The pots were covered with plastic bags which were removed when the plants were clearly growing—after about ten days.

Plants were grown under a 16:8-hour photoperiod, with a daytime temperature of 23° C. and a nightime temperature of 17° C. When the primary flowering stem began to elongate, it was covered with a mesh pollen-containment bag to prevent outcrossing. Self-pollination was facilitated by shaking the plants several times each day. Seeds derived from self-pollinations were harvested about three months after planting.

Media
Minimal A Bacterial Growth Medium
  Dissolve in distilled water:
  10.5 grams potassium phosphate, dibasic
  4.5 grams potassium phosphate, monobasic
  1.0 gram ammonium sulfate
  0.5 gram sodium citrate, dihydrate
  Make up to 979 mLs with distilled water
  Autoclave
  Add 20 mLs filter-sterilized 10% sucrose Add 1 mL filter-sterilized 1M MgSO$_4$ Brassica Callus Medium BC-28

Per liter:

Murashige and Skoog Minimal Organic Medium (MS salts, 100 mg/L i-inositol, 0.4 mg/L thiamine; GIBCO #510–3118)

30 grams sucrose 18 grams mannitol 1.0 mg/L 2,4-D 0.3 mg/L kinetin 0.6% agarose pH 5.8

Brassica Regeneration Medium BS-48

Murashige and Skoog Minimal Organic Medium

Gamborg B5 Vitamins (SIGMA #1019)

10 grams glucose 250 mg xylose 600 mg MES 0.4% agarose pH 5.7

Filter-sterilize and add after autoclaving:

2.0 mg/L zeatin 0.1 mg/L IAA

Brassica Shoot Elongation Medium MSV-1A

Murashige and Skoog Minimal Organic Medium

Gamborg B5 Vitamins 10 grams sucrose 0.6% agarose pH 5.8

EXAMPLE 6

Analysis of Transgenic *Brassica napus* Plants

Successful insertion of the intact, sense β-ketoacylsynthetase II transcriptional unit was verified by Southern analysis using leaf tissue as the source of DNA. Genomic DNA was isolated from tranformed canola leaves of the surviving plants described below and digested with Kpn I/Sal I. Southern analysis was done as in Example 3 using the β-ketoacylsynthetase II coding sequence as the probe template. The Southern blots revealed that all surviving plants (plant numbers 9, 13, 16, 25, 29, 30, 31, 33, 45, 46, 56, 57, 67, 70, 78, 80, 92, 94, 12 and 180) transformed with the KAS II binary vector contained introduced copies of the soybean β-ketoacylsynthetase II with the exception of plants 9 and 13. Under the hybridization conditions described in Example 3, the soybean β-ketoacylsynthetase II did net react with the endogenous canola β-ketoacylsynthetase II in control (plant 199) and transgenic plants. All plants except 9 and 13 had at least one copy of the soybean β-ketoacylsynthetase II cDNA which was not rearranged from the introduced construction. Plants 16, 29, 25, 30, 31, 80 and 92 had multiple inserts of the soybean β-ketoacylsynthetase II cDNA.

Alteration of fatty acid content in seeds of transformed plants was observed by determining the relative content of the five most abundant fatty acids in individual *Brassic napus* seeds taken from transformed plant 25, which was shown to contain the intact, sense insert by Southern analysis. Comparison of these fatty acid profiles to those from plant 199 transformed with the selection cassette pZS199 and grown under the same conditions was the basis for assessment of an effect of the introduced gene.

The relative content of individual fatty acids in single *Brassica napus* seeds was determined by gas liquid chromatography after formation of the fatty acid methyl esters. Fatty acid analysis was performed on single seeds of plant 25 to observe the effect of genetic segregation for the introduced gene on the fatty acid profile. Individual Brassica seeds were ground in liquid N$_2$ and transesterified to methanol in 0.5 mL of 1% sodium methoxide in methanol. One mL of a saturated NaCl solution was added and the fatty acid methyl esters were extracted into diethyl ether. The ether solutions were taken to dryness under an N$_2$ stream and the extracted methyl esters were re-dissolved in 200 μl of hexane for analysis by GLC. GLC separations were done isothermally at 185° on a fused silica capillary column (stationary phase, SP-2330, 30M in length, Supelco, Bellefonte, Pa.). Data were analyzed by integration of peak area to determine the relative contribution of each of the 5 most prominent fatty acids in soybean triacylglycerol. The relative contributions of individual fatty acids to the total fatty acid profile of individual seeds from one of the transformed plants, number 25, and the mean value of seven seeds taken from the control plant (199), which was transformed with the pZS199 vector described, are given in Table 2 below.

TABLE 2

| SEED # | % OF TOTAL FATTY ACIDS | | | | |
|---|---|---|---|---|---|
| | 16:0 | 18:0 | 18:1 | 18:2 | 18:3 |
| 25-1 | 4.82 | 1.09 | 67.3 | 21.5 | 5.30 |
| 25-2 | 4.61 | 1.11 | 68.0 | 21.2 | 5.14 |
| 25-3 | 3.53 | 2.95 | 71.0 | 17.0 | 5.46 |
| 25-4 | 4.27 | 2.18 | 64.0 | 23.1 | 6.45 |
| 25-5 | 4.17 | 5.16 | 67.6 | 14.6 | 8.54 |
| 25-6 | 4.51 | 4.25 | 63.6 | 22.0 | 8.06 |
| 25-7 | 4.04 | 4.20 | 66.7 | 17.3 | 7.70 |
| 25-8 | 3.68 | 2.02 | 68.6 | 20.1 | 5.61 |
| 25-9 | 3.95 | 2.53 | 66.7 | 20.9 | 5.88 |
| 25-10 | 4.31 | 2.73 | 66.5 | 19.6 | 6.86 |
| 25-11 | 5.22 | 4.04 | 62.4 | 19.5 | 8.87 |
| 25-12 | 5.20 | 3.85 | 57.5 | 23.4 | 10.1 |
| 25-13 | 4.72 | 3.39 | 67.7 | 17.3 | 6.90 |
| 25-14 | 4.54 | 2.44 | 60.6 | 24.0 | 8.40 |
| 25-15 | 4.37 | 4.37 | 69.3 | 16.6 | 5.34 |
| 25-16 | 4.58 | 1.63 | 71.5 | 18.3 | 4.06 |
| 25-mean | 4.41 | 3.00 | 66.2 | 19.8 | 6.79 |
| SD (n = 16) | 0.48 | 1.23 | 3.7 | 2.7 | 1.67 |
| 199-mean | 5.20 | 2.17 | 61.4 | 20.1 | 5.65 |
| SD (n = 7) | 0.70 | 0.89 | 5.3 | 3.5 | 1.49 |

Seeds from plant 25 had a range of 16:0 contents from 3.53% (seed 25-3), which was 1% lower than the lowest control 16:0 content,to 5.22% (plant 25-11), which was similar to the control mean. The midrange value (e.g., seed 25-10) was 4.31. A lower 16:0 content was reflected by an increased 18:0 and 18:1 content and thus the differences in 16:0 content were reflected by the differences in the (18:0+ 18:1)/16:0 ratio among different seeds as shown in Table 3:

TABLE 3

| SEED | % 16:0 | (18:0 + 18.1)/16.0 |
|---|---|---|
| 25-3 | 3.53 | 21.0 |
| 25-10 | 4.31 | 16.1 |
| 25-11 | 5.22 | 12.7 |
| 25-mean | 4.41 | 15.7 |
| 119-mean | 5.20 | 12.2 |

Thus sense expression of soybean β-ketoacylsynthetase II in canola resulted in a decrease in 16:0 content and a concomitant increase in both 18:0 and 18:1 content.

EXAMPLE 7

Agrobacterium Mediated Transformation of Tobacco

The binary vector, pZSKS II, constructed by insertion of embryo specific promoters driving the sense expression of β-ketoacylsynthetase II into pZS199 was transferred by a freeze/thaw method [Holsters et al. (1978) Mol Gen Genet 163:181–187] to the Agrobacterium strain LBA4404/pAL4404 [Hockema et al. (1983), Nature 303:179–180]. The Agrobacrerium transformants were used to inoculate tobacco leaf disks [Horsch et al. (1985) Science 227:1229–1231]. Transgenic plants were regenerated in selective media containing kanamycin. *Brassica napus* transformation.

EXAMPLE 8

Analysis of Transgenic Tobacco Plants

Successful insertion of the intact, sense β-ketoacylsynthetase II transcriptional unit was verified by Southern analysis using tobacco leaf tissue as described in Example 6 above. The Southern blots revealed that all surviving plants (plant numbers 8A, 11B, 15B, 20C, 22D, 24A, 26C, 28A, 29B, 37A, 44A, 45A, 51A, 52C, 58B, 59B, 61A, 66C, 71A 78A) transformed with the KAS II binary vector contained introduced copies of the soybean β-ketoacylsynthetase II with the possible exception of plants 51A and 71A. All plants except 51A and 71A had at least one copy of the soybean β-ketoacylsynthetase II cDNA which was not rearranged from the introduced construction. Plants 11B, 44A and 66C had multiple inserts of the soybean β-ketoacylsynthetase II cDNA.

Alteration of fatty acid content in seeds of transformed plants was observed by determining the relative content of the five most abundant fatty acids in pooled seeds from individual plants by the methods described in Example 5. The relative 16:0 content of bulk seeds from plants 11B, 15B, 44A, 61A, 66C were each compared with that of plants 51A and 71A, which do not appear to contain the soybean β-ketoacylsynthetase II cDNA but have been exposed to identical conditions as the plants that do and therefore serve as a useful control. The fatty acid content of plants 194A, 194B and 194C which were transformed with a pZS199 vector without the β-ketoacylsynthetase cDNA, were also compared to the other plants. The 16:0 content of bulk seeds, shown as a percentage of the total of the five major fatty acids, and the ratio of 18:0+18:1 to 16:0 are shown in Table 4 below. The content of 18:2 (76.0%±0.5%) and 18:3 (1.29±0.1%) was similar in all plants.

TABLE 4

| Plant | % 16:0 | % 18:0 | % 18:1 | Ratio (18:0 + 18:1/16:0) |
|---|---|---|---|---|
| Control Plants: | | | | |
| 194A | 10.89 | 2.20 | 10.27 | 1.14 |
| 194B | 12.98 | 2.72 | 10.68 | 1.03 |
| 194C | 11.03 | 2.21 | 10.13 | 1.20 |
| average | 11.63 | 2.34 | 10.36 | 1.12 |

TABLE 4-continued

| Plant | % 16:0 | % 18:0 | % 18:1 | Ratio (18:0 + 18:1/16:0) |
|---|---|---|---|---|
| Southern Blot Negative: | | | | |
| 71A | 11.54 | 2.05 | 8.65 | 0.93 |
| 51A | 9.76 | 2.28 | 10.29 | 1.29 |
| average | 10.65 | 2.17 | 9.47 | 1.11 |
| Southern Blot Positive: | | | | |
| 15B | 9.91 | 2.24 | 10.11 | 1.25 |
| 58B | 9.94 | 2.19 | 10.87 | 1.31 |
| 29B | 9.85 | 2.21 | 9.73 | 1.21 |
| 37A | 10.93 | 2.40 | 10.27 | 1.17 |
| 8A | 10.37 | 2.14 | 10.08 | 1.17 |
| 20C | 9.80 | 2.24 | 10.36 | 1.29 |
| 22D | 9.78 | 2.50 | 11.07 | 1.39 |
| 24A | 10.32 | 2.16 | 10.06 | 1.18 |
| 26C | 9.95 | 2.29 | 10.48 | 1.28 |
| 28A | 10.29 | 2.31 | 9.84 | 1.18 |
| 45A | 10.09 | 2.22 | 10.14 | 1.23 |
| 52C | 10.91 | 2.21 | 9.46 | 1.07 |
| 61A | 9.69 | 2.27 | 10.17 | 1.28 |
| 78C | 10.35 | 2.11 | 10.33 | 1.20 |
| average | 9.75 | 2.25 | 10.21 | 1.23 |
| Southern Blot Positive (Multiple Copies): | | | | |
| 11B | 9.55 | 2.34 | 9.65 | 1.26 |
| 66C | 10.04 | 2.18 | 10.43 | 1.26 |
| 44A | 8.74 | 2.56 | 9.80 | 1.42 |
| average | 9.44 | 2.36 | 9.96 | 1.31 |

Plant 44A showed the lowest relative 16:0 content, with the pool of seeds from this plant analysed showing a relative 16:0 content of 8.74%. Since the bulk seed analysis represents an average fatty-acid content of a segregating population, individual seeds from plants 44A, 51A and 15B were analyzed for lipid content as described in Example 5. The % 16:0 content of individual seeds from each of the three plants, ranked from the lowest to the highest is shown in Table 5 below:

TABLE 5

| Seed # | Plant 44A % 16:0 | Plant 15B % 16:0 | Plant 51A % 16:0 |
|---|---|---|---|
| 1 | 6.36 | 9.29 | 9.90 |
| 2 | 7.89 | 9.48 | 9.93 |
| 3 | 9.08 | 9.65 | 9.97 |
| 4 | 9.24 | 9.70 | 10.00 |
| 5 | 9.27 | 9.71 | 10.20 |
| 6 | 9.45 | 9.75 | 10.23 |
| 7 | 9.50 | 9.80 | 10.42 |
| 8 | 9.53 | 9.85 | 10.43 |
| 9 | 9.58 | 9.85 | 10.48 |
| 10 | 9.59 | 9.89 | 10.58 |
| 11 | 9.60 | 9.96 | 10.61 |
| 12 | 9.62 | 9.96 | 10.72 |
| 13 | 9.71 | 10.09 | 10.75 |
| 14 | 9.72 | 10.24 | 10.78 |
| 15 | 9.74 | 10.27 | 10.83 |
| 16 | 9.74 | 10.32 | 10.94 |
| 17 | 9.79 | 10.46 | 10.98 |
| 18 | 9.80 | 10.57 | 11.15 |
| 19 | 10.07 | n.d. | 11.71 |
| average | 9.32 | 9.94 | 10.56 |
| SD | 0.85 | 0.34 | 0.47 |

The lowest observed % 16:0 content (6.76%) was in one of the seeds from plant 44a which has multiple copies of β-ketoacylsynthetase. The lowest observed 16:0 content in plant 15B, which has at least one copy of the β-ketoacylsynthetase cDNA, was 9.29% which was lower than the lowest value observed (9.90%) in the control plant 51A. The highest observed % 16:0 content in a seed from plant 44A (10.07%) overlaps only with the very lowest values observed in seeds from plant 51A. Thus, the effect of the β-ketoacylsynthetase cDNA has been to reduce the % 16:0 content of tobacco seeds from an average of about 10.5%, and an high value of 11.7%, to an average of 9.32% and down to as little as 6.36%. Seeds from plant 44A will be grown to mature plants and bulk fatty analysis of the seeds of these mature plants will be measured. Based on the seed analysis above, plants that derive from an homozygous seed of plant 44A should have an average bulk % 16:0-content of 6 to 8% in their seed.

EXAMPLE 9

Construction of Vectors for Transformation of *Glycine max* for Reduced Expression of β-ketoacylsynthetase in Developing Seeds β-ketoacylsynthetase cDNA sequences under control of the β-conglycinin promoter were constructed using the vector pM109A described in Example 4 above. For use, in the soybean transformation system described below, the transcriptional unit was placed in vector pML45, which consists of the non-tissue specific and constitutive promoter designated 508D and described in Hershey (WO 9011361) driving expression of the neomycin phosphotransferase gene described in (Beck et al. (1982) Gene 19:327–336) followed by the 3' end of the nopaline synthase gene including nucleotides 848 to 1550 described by (Depicker et al. (1982) J. Appl. Genet. 1:561–574). This transcriptional unit was inserted into the commercial cloning vector pGEM9Z (Promega) and is flanked at the 5' end of the 508D promoter by the restriction sites Sal I, Xba I, Bam HI and Sma I in that order. An additional Sal I site is present at the 3' end of the NOS 3' sequence and the Xba I, Bam HI and Sal I sites are unique.

Removal of the unit [β-conglycinin promter:cloning region :phaseolin 3' end] from pM109A by digestion with Hind III, blunting the ends with Klenow and isolating the 1.8 kB fragment affords the expression cassette pCST by ligating the above isolated fragment into the Sma I site of pML45. The pCST vector has a unique Sma I site between the β-conglycinin promoter and the 3' phaseolin end.

The modified 2.2 kb cDNA encoding the soybean β-ketoacylsynthetase II described in Example 4 was cloned, in the sense oreintation, into the Sma I site of pCST to give a selectable expression vector, pCSKSST, for use in the soybean transformation system described in Example 10 below. The orientation of the insert in the sense direction in pCSKSST was checked by digestion of pCSKSST with Eco RI and Spe I.

EXAMPLE 10

Transformation of Somatic Soybean Embryo Cultures

Soybean embryogenic suspension cultures were maintained in 35 mL liquid media (SB55) on a rotary shaker, 150 rpm, at 28° C. with mixed florescent and incandescent lights on a 16:8 hour day/night schedule. Cultures were subcultured every two weeks by inoculating approximately 35 mg of tissue into 35 mL of liquid medium.

Soybean embryogenic suspension cultures were transformed by the method of particle gun bombardment (see Klein et al. (1987) Nature (London) 327:70). A DuPont Biolistic PDS1000/HE instrument (helium retrofit) was used for these transformations.

To 50 μL of a 60 mg/mL 1 μm gold particle suspension was added (in order); 5 μL DNA (1 μg/μL), 50 μL $CaCl_2$ (2.5M), and 20 μL spermidine (0.1M). The particle preparation was agitated for three min, spun in a microfuge for 10 sec and the supernatant removed. The DNA-coated particles were then washed once in 400 μL 70% ethanol and resuspended in 40 μL of anhydrous ethanol. The DNA/particle suspension was sonicated three times for one sec each. Five μL of the DNA-coated gold particles were then loaded on each macro carrier disk.

Approximately 800–950 mg of a two week old suspension culture was placed in an empty 60×15 mm petri dish and the residual liquid removed from the tissue with a pipette. For each transformation experiment, approximately 5–10 plates of tissue were normally bombarded. Membrane rupture pressure was set at 1100 psi and the chamber evacuated to a vacuum of 28" mercury. The tissue was placed approximately 3.5" away from the retaining screen and bombarded three times. Following bombardment, the tissue was placed back into liquid and cultured as described above.

Thirteen days post bombardment, the liquid media was exchanged with fresh SB55 containing 50 mg/mL hygromycin. The selective media was refreshed weekly. At four, six and seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus, each new line was treated as an independent transformation event.

To regenerate whole plants, embryonic clusters were removed from liquid culture and placed in 35 mL of liquid media (SB103) or on a solid agarose media (SB148) with no hormones or antibiotics. For liquid maturation, embryonic clusters were cultured in flasks on a rotary shaker (150 rpm) at 26° C. with mixed fluorescent and incandescent light on a 16 h. day/8 h. night schedule. Embryos matured on agarose were cultured at 26° C. with mixed fluorescent and incandescent light on a 16 h. day/8 h. night schedule. Embryos were cultured for 4 weeks and then samples from each individual line analyzed for fatty acid composition as described below (Example 11). After a further four weeks, embryos were ready for germination.

Media:
SB55 Stock Solutions (grams per Liter):

| MS Sulfate 100X Stock | | B5 Vitamin Stock | |
|---|---|---|---|
| $MgSO_4$ $7H_2O$ | 37.0 | 10 g m-inositol | |
| $MnSO_4$ $H_2O$ | 1.69 | 100 mg nicotinic acid | |
| $ZnSO_4$ $7H_2O$ | 0.86 | 100 mg pyridoxine HCl | |
| $CuSO_4$ $5H_2O$ | 0.0025 | 1 g thiamine | |
| MS Halides 100X Stock | | SB55 (per liter) | |
| $CaCl_2$ $2H_2O$ | 44.0 | 10 mL each MS stocks | |
| KI | 0.083 | 1 mL B5 Vitaimin stock | |
| $CoCl_2$ $6H_2O$ | 0.00125 | 0.8 g $NH_4NO_3$ | |
| $KH_2PO_4$ | 17.0 | 3.033 g $KNO_3$ | |
| $H_3BO_3$ | 0.62 | 1 mL 2,4-D (10 mg/mL stock) | |
| $Na_2MoO_4$ $2H_2O$ | 0.025 | 60 g sucrose | |
| | | 0.667 g asparagine | |
| | | pH 5.7 | |
| MS FeEDTA 100X Stock | | SB103 (per liter) | |
| $Na_2EDTA$ | 3.724 | MS Salts | |
| $FeSO_4$ $7H_2O$ | 2.784 | 6% maltose | |
| | | B5 vitamins | |
| SB148 (per liter) | | pH 5.7 | |
| MS salts | | | |
| 6% maltose | | | |

B5 vitamins
0.7% agarose
pH 5.7

EXAMPLE 11

Analysis of Transgenic Glycine max Plants

While in the globular embryo state in liquid culture as described in Example 10, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominant seed proteins (a' subunit of β-conglycinin, Kunitz Trypsin Inhibitor III and Soybean Seed Lectin) are essentially absent. Upon transfer to hormone-free media to allow differentiation to the maturing somatic embryo state as described in Example 10, triacylglycerol becomes the most abundant lipid class. Also, mRNAs for a'-subunit of β-conglycinin, Kunitz Trypsin Inhibitor III and Soybean Seed Lectin become very abundant messages in the total mRNA population. In these respects the somatic soybean embryo system behaves very similarly to maturing zygotic soybean embryos in vivo, and is therefore a good and rapid model system for analyzing the phenotypic effects of modifying the expression of genes in the fatty acid biosynthesis pathway. Similar somatic embryo culture systems have been documented and used in another oilseed crop, rapeseed (Taylor et al. (1990) Planta 181:18–26).

Southern analysis for the presence of the intact, introduced sense construction may be performed as described in Example 6 using groups of embryos from a single transformation event. Fatty acid analysis was performed as described in Example 6 using single embryos as the tissue source. A number of embryos from two lines, 2872 and 3015, were analyzed for fatty acid content. The relative fatty-acid composition of embryos taken from tissue transformed with pCKSST was compared with control tissue, transformed with pCST, from the same lines. The results of this analysis are shown in Table 6 below.

TABLE 6

| | 16:0 | 18:0 | 18:1 | 18:2 | 18:3 |
|---|---|---|---|---|---|
| | | relative fatty acid content (%) | | | |
| Line 2872-control embryos | | | | | |
| 2872-C1 | 13.32 | 12.84 | 51.88 | 12.01 | 2.72 |
| 2872-C2 | 13.03 | 18.50 | 51.26 | 11.57 | 0.20 |
| 2872-C3 | 12.95 | 22.45 | 46.82 | 11.07 | 0.10 |
| average | 13.10 | 17.93 | 50.00 | 11.55 | 1.00 |
| Line 2872-310/8/1 (β-ketoacylsynthetase II) embryos | | | | | |
| 310/8/1-1 | 14.21 | 8.74 | 51.89 | 15.30 | 0.13 |
| 310/8/1-2 | 14.21 | 11.00 | 53.38 | 12.90 | 0.10 |
| 310/8/1-3 | 16.30 | 8.65 | 47.00 | 17.47 | 0.15 |
| average | 14.91 | 9.46 | 50.76 | 15.22 | 0.12 |
| Line 2872-310/8/14 (β-ketoacylsynthetase II) embryos | | | | | |
| 8/14-1 | 13.75 | 21.80 | 45.61 | 11.39 | 0.10 |
| 8/14-2 | 14.97 | 25.06 | 39.22 | 12.60 | 0.10 |
| 8/14-3 | 15.81 | 8.53 | 45.93 | 20.44 | 0.15 |
| average | 14.83 | 18.46 | 43.56 | 14.81 | 0.13 |

TABLE 6-continued

| | 16:0 | 18:0 | 18:1 | 18:2 | 18:3 |
|---|---|---|---|---|---|
| | | relative fatty acid content (%) | | | |
| Line 3015-controls | | | | | |
| 3015-1 | 10.15 | 15.20 | 49.20 | 9.58 | 2.90 |
| 3015-2 | 11.96 | 21.83 | 53.11 | 7.97 | 0.53 |
| 3015-3 | 11.48 | 26.47 | 48.06 | 8.16 | 0.96 |
| average | 11.20 | 21.17 | 50.12 | 8.57 | 1.46 |
| line 3015-310/3/2 | | | | | |
| 3/2-1 | 17.03 | 20.46 | 41.14 | 14.69 | 0.65 |
| 3/2-2 | 16.32 | 17.04 | 39.01 | 20.47 | 1.24 |
| 3/2-3 | 17.72 | 22.76 | 40.22 | 12.43 | 0.69 |
| average | 17.02 | 20.09 | 40.12 | 15.86 | 0.86 |

In line 2872 no embryo has yet been analyzed with a fatty acid profile much different from that of the control tissue. In line 3015 however, the β-ketoacylsynthetase II line 3015–310/3/2 has 17% 16:0 compared with about 11% in the 3015 control. This phenotype probably results from the inhibition of β-ketoacylsynthetase II activity due to cosuppression of the transgene and the homologous, endogenous soybean gene. The phenomenon of cosuppression is discussed above. The increase in 16:0 is reflected by a decrease in 18:1. Thus, the (18:0+18:1)/16:0 ratio is 6.37 in the control and 3.54 in line 3015–310/3/2. There is an unaccountable increase in 18:2 in the β-ketoacylsynthetase II embryo and the 18:3 content is reduced.

Line 3015–310/3/2 and other useful transformation lines identified by these methods can be carried through to fertile plants by known cultivation methods.

EXAMPLE 12

Construction of a Vector for Transformation of Zea mays for Increased Expression of β-ketoacylsynthetase II in Developing Seeds A useful promoter for the seed specific expression of β-ketoacylsynthetase II in maize (Zea mays) would be the promoter for the gene encoding the 18 kD maize oleosin (Huang,(1992) Ann. Rev. Plant Physiol. Plant. Mol. Biol., 43:177–200). The cloning of this gene has been described (Qu and Huang, (1990) J. Biol. Chem., 265:2238–2243) and the complete genomic DNA sequence is availble in the GenBank database (Accession number J05212). Part of the 5' non-coding region (nucleotides 353 to 1485 of the sequence J05212 in GenBank) of the 18 kD oleosin gene may be amplified by PCR using oligonucleotide primers based on this nucleotide sequence and maize genomic DNA for the template (Ausubel et al., Current Protocols in Molecular Biology (1989) John Wiley & Sons). The sense (5') primer would contain the sequence of nucleotides contained in nucleotides 353–374 of the oleosin sequence contained in Genbank J05212. The sense primer would also contain nucleotides encoding a Hind III restriction site (Ausubel et al., Current Protocols in Molecular Biology (1989) John Wiley & Sons) with 7 extra nucleotides (GAGAAAG), 5' to the Hind III nucleotides, at the 5' end of the primer. The antisense (3') primer would contain nucleotides which are the exact complement of the nucleotides contained in nucleotides 1466 to 1485 of the oleosin seqeunce contained in Genbank J05212. The antisense primer would also contain nucleotides encoding an Nco I restriction site (Ausubel et al., Current Protocols in Molecular Biology (1989) John Wiley & Sons) and an additional 7 nucleotides (GAGAAAG), 5' to the Nco I nucelotides, at the 5' end of the primer. The final G nucleotide of the Nco I site is contained in the complement of nucleotide 1485 of the oleosin gene and not included in the antisense primer. The amplified 1138 kb product may be digested with Hind III and Nco I and gel-purified.

β-ketoacylsynthetase II cDNA sequences under control of the maize 18 kD oleosin promoter may be constructed using the vector pCW109 described in Example 4 above. The vector pCW109 can be digested with Hind III and Nco I to release the 555 bp β-conglycinin promoter and the resulting vector fragment (pCW109-G') can be gel purified. The 1138 kb Hind III/Nco I fragment of the maize oleosin promoter can be ligated into the Hind III/Nco I sites of pCW109-G⁻ to give the plasmid pMOL109. To facilitate use in sense constructions, the Nco I site and potential translation start site in the plasmid pMOL109 may be destroyed by digestion with Nco I, mung bean exonuclease digestion and re-ligation of the blunt site to give the modified plasmid pMOL109A.

The oleosin promoter:phaseolin 3' end may be released from the modified pMOL109A by Hind III digestion, filled in by reaction with Klenow, isolated and ligated into the Sma I site of pUC17 (Stratagene) to give the modified plasmid pCMOL. The modified 2.2 kb cDNA encoding the soybean β-ketoacylsynthetase II may be then ligated into the Sma I site of pCMOL to yield the plasmid pCMOLKS II. The sense orientation of the insert may be checked by digestion of pCMOLKS II with Eco RI (vectors with a sense KAS II should yield a 0.9 kb fragment).

EXAMPLE 13

Transformation of Maize

Immature embryos may be dissected from developing maize caryopses derived from crosses of the inbred lines A188 and B73. The embryos are isolated 10 to 11 days after pollination when they are, 1.0 to 1.5 mm long. The embryos are then placed with the axis-side facing down and in contact with agarose-solidified N6 medium (Chu et al. (1975), Sci. Sin. Peking 18:659) and are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant is cultured on N6 medium and subcultured on this medium every 2 to 3 weeks.

The plasmid, pBARGUS, used for transformation has been previously described (Fromm et al. (1990) Biotechnology 8:833). This plasmid contains the bar gene (EP 242236) which encodes phosphinothricin acetyl trasnsferase (PAT). The enzyme PAT confers resistance to herbicidal glutamine synthetase inhibitors such as phosphinothricin. The bar gene is under the control of the 35S promoter from Cauliflower Mosaic Virus [Odell et al., (1985) Nature 313:810–812] and the 3' region of the nopaline synthase gene from the T-DNA of the Ti plasmid of Agrobacterium tumefaciens. This plasmid also contains a gene that uses the promoter from the alcohol dehydrogenase gene from maize and the 3' region of the nopaline synthase gene to express a β-glucuronidase coding region. The β-ketoacylsynthetase II cDNA fragment may be delivered on a second plasmid, pCMOLKS II, described in example 12 above.

The particle bombardment method (Klein et al. (1987), Nature 327:70) may be used to transfer genes to the callus culture cells. Gold particles (1 μm in diameter) are coated with DNA using the following technique. Plasmid DNA (10 μg of pBARGUS and 10 μg of pCMOLKS II; each at a concentration of 1 μg of μL) is added to 50 μL of a suspension of gold particles (60 mg per mL). Calcium chloride (50 μL of a 2.5M solution) and spermidine free base (20 μL of a 1.0M solution) are then added to the particles. The suspension is vortexed during the addition of these solutions. After 10 min., the tubes are briefly centrifuged (5 sec at 15,000 rpm) and the supernatant removed with a pipetman. The particles are resuspended in 200 μL of ethanol, centrifuged again and the supernatant removed. The ethanol rinse is performed again and the particles resuspended in a final volume of 30 μL of ethanol. An aliquot (5 μL) of the DNA-coated gold particles is placed in the center of a Kapton™ flying disc (Bio-Rad Labs). The particles are accelerated into the corn tissue using a helium pressure of 1000 psi, a gap distance of 0.5 cm and a flying distance of 1.0 cm. A Biolistic™ PDS-1000/He (Bio-Rad Instruments, Hercules, Calif.) can be used for these experiments.

About 200 small clusters (2 to 3 mm in diameter) of embryogenic callus are arranged on the surface of agarose-solidified N6 medium contained in a petri dish. The tissue will cover a circular area of about 6 cm in diameter. The petri dish containing the tissue is placed in the chamber of the PDS-1000/He and the air in the chamber is evacuated to a vacuum of 28 in of Hg. The macrocarrier is accelerated with a helium shock wave using a rupture membrane that bursts when the He pressure in the shock tube reaches 1000 psi. The tissue is placed approximately 8 cm from the stopping screen. Ten plates of tissue are usually bombarded with the DNA-coated gold particles.

Seven days after bombardment the tissue can be transferred to N6 medium that contains phosphinothricin (2 mg per liter) and lacks casein or proline. The tissue will continue to grow slowly on this medium. After an additional 2 weeks the tissue may be transferred to fresh N6 medium containing chlorsulfuron. After 6 weeks, areas of about 1 cm in diameter of actively growing callus will be identified on some of the plates containing the phosphinothricin-supplemented medium. These calli will continue to grow when subcultured on the selective medium. Clusters of tissue may be transferred to N6 medium supplemented with 0.2 mg per liter of 2,4-D. After two weeks the tissue can be transferred to regeneration medium (Fromm et al., (1990) Biotechnology 8:833). Regenerated plantlets can be transferred to pots grown into mature plants.

| N6 Medium | |
|---|---|
| Component | Quantity per liter |
| Solution I | 10.0 mL |
| CaCl$_2$ (1M) | 1.25 mL |
| Solution III | 10.0 mL |
| MgSO$_4$ (1M) | 0.75 mL |
| Solution V | 1.0 mL |
| Vitamin Stock | 1.0 mL |
| Casein hydrolysate | 0.1 g |
| Sucrose | 60.0 g |
| Myo-inositol | 0.1 g |
| 2,4-D (2 mg/mL stock) | 0.5 mL |
| pH to 5.8 | |
| Add 6 g of agarose for plates | |
| Solution I | |
| (NH$_4$)$_2$SO$_4$ | 23.0 g |
| KNO$_3$ | 141.5 g |
| KH$_2$PO$_4$ | 20.0 g |
| H$_2$O | 500.0 mL |

-continued

N6 Medium

| Component | Quantity per liter |
| --- | --- |
| Solution III | |
| Na$_2$EDTA | 1.85 g |
| FeSO$_4$.7H$_2$O | 1.35 g |
| H$_2$O | 500.0 mL |
| Solution V: | |
| H$_3$BO$_3$ | 0.16 g |
| MnSO$_4$.H$_2$O | 0.33 g |
| ZnSO$_4$.7H$_2$O | 0.15 g |
| KI | 0.08 g |
| Na$_2$MoO$_4$.2H$_2$O | 0.025 g |
| CuSO$_4$.5H$_2$O | 0.0025 g |
| CoCl$_2$.2H$_2$O | 0.0025 g |
| H$_2$O | 100.0 mL |
| Vitamin Stock | |
| niacin | 0.13 g |
| thiamine | 0.025 g |
| pyridoxine | 0.025 g |
| calcium pantothenate | 0.025 g |
| H$_2$O | 100.0 mL |

EXAMPLE 14

CLONING OF β-KETOACYLSYNTHETASE II cDNAs FROM OTHER SPECIES USING THE SOYBEAN β-KETOACYLSYNTHETASE II CLONE AS A HYBRIDIZATION PROBE

The cDNA insert from plasmid pC16 was removed from the Bluescript vector by digestion with restriction enzyme Eco RI in standard conditions as described in Sambrook et al. (Molecular Cloning, A Laboratory Manual, 2nd ed. (1989) Cold Spring Harbor Laboratory Press). This fragment, or the modified 2.2 kb β-ketoacylsynthetase cDNA described in Example 4, may be labeled with 32p using a Random Priming Kit from Bethesda Research Laboratories under conditions recommended by the manufacturer. The resulting radioactive probe can be used as a probe to isolate homologous genes from other species.

Cloning of a *Brassica napus* Seed cDNA Encoding β-ketoacylsynthetase II

The radiolabelled 2.2 kb β-ketoacylsynthetase cDNA probe was used to screen a *Brassica napus* seed cDNA library. In order to construct the library, *Brassica napus* seeds were harvested 20–21 days after pollination, placed in liquid nitrogen, and polysomal RNA was isolated following the procedure of Kamalay et al., (Cell (1980) 19:935–946). The polyadenylated mRNA fraction was obtained by affinity chromatography on oligo-dT cellulose (Aviv et al., Proc. Natl. Acad. Sci. USA (1972) 69:1408–1411). Four micrograms of this mRNA were used to construct a seed cDNA library in lambda phage (Uni-ZAP™ XR vector) using the protocol described in the ZAP-cDNA™ Synthesis Kit (1991 Stratagene Catalog, Item #200400). Approximately 300,000 clones were screened for positively hybridizing plaques using the radiolabelled 2.2 kb β-ketoacylsynthetase cDNA as a probe essentially as described in Sambrook et al., (Molecular Cloning: A Laboratory Manual, 2nd ed. (1989) Cold Spring Harbor Laboratory Press) except that low stringency hybridization conditions (50 mM Tris, pH 7.6, 6× SSC, 5× Denhardt's, 0.5% SDS, 100 µg denatured calf thymus DNA and 50° C.) were used and post-hybridization washes were performed twice with 2× SSC, 0.5% SDS at room temperature for 15 min, then twice with 0.2× SSC, 0.5% SDS at room temperature for 15 min, and then twice with 0.2× SSC, 0.5% SDS at 50° C. for 15 min. A positive plaque showing strong hybridization was picked, plated out, and the screening procedure was repeated. From the secondary screen a pure phage plaque was isolated. A plasmid clone containing the cDNA insert was obtained through the use of a helper phage according to the in vivo excision protocol provided by Stratagene. Double-stranded DNA was prepared using the alkaline lysis method as previously described, and the resulting plasmid was size-analyzed by electrophoresis in agarose gels. The clone, designated pCK146, contained an approximately 1.8 kb insert. This insert may be sequenced as described above in Example 1.

What is claimed is:

1. An isolated nucleic acid fragment comprising a nucleotide sequence encoding a soybean seed β-ketoacyl-ACP synthetase II enzyme, said sequence corresponding to nucleotides 1 to 2675 of SEQ ID NO:1, or to any nucleotide sequence which encodes the amino acid sequence of said enzyme, or to any nucleotide sequence encoding said enzyme in which one or more amino acid substitutions have been made that do not affect the functional properties of the encoded enzyme.

2. An isolated nucleic acid fragment comprising a nucleotide sequence which encodes the soybean seed β-ketoacyl-ACP synthetase II enzyme precursor, said sequence corresponding to nucleotides 218 to 2675 of SEQ ID NO:1, or any to any nucleotide sequence which encodes the amino acid sequence of said enzyme precursor, or to any nucleotide sequence encoding said enzyme precursor in which one or more amino acid substitutions have been made that do not affect the functional properties of the encoded enzyme precursor.

3. An isolated nucleic acid fragment comprising a nucleotide sequence which encodes the mature soybean seed β-ketoacyl-ACP synthetase II enzyme, said sequence corresponding to nucleotides 311 to 2675 of SEQ ID NO:1, or to any nucleotide sequence which encodes the amino acid sequence of said mature enzyme, or to any nucleotide sequence encoding said mature enzyme in which one or more amino acid substitutions have been made that do not affect the functional properties of the encoded mature enzyme.

4. A chimeric gene capable of transforming a plant cell comprising a nucleic acid fragment of claim 1 operably linked to suitable heterologous regulatory sequences, the chimeric gene causing altered levels of soybean seed β-ketoacyl-ACP synthetase II in the transformed seed.

5. A chimeric gene capable of transforming cells of microorganisms comprising a nucleic acid fragment of claim 3 operably linked to suitable regulatory sequences, said gone causing the expression of said mature soybean seed β-ketoacyl-ACP synthetase II enzyme in the microorganism.

6. A method of producing seed oil containing altered levels of palmitic and stearic acids comprising:

(a) transforming a plant cell of an oil-producing species with a chimeric gene of claim 4, (b) growing fertile plants from the transformed plant cells of step (a), (c) screening progeny seeds from the fertile plants of step (b) for the desired levels of palmitic and stearic acids, and (d) processing the progeny seed of step (c) to obtain seed oil containing altered levels of palmitic and stearic acids.

7. The method of claim 6 wherein said plant cell of an oil-producing species is selected from the group consisting of soybean, oilseed Brassica species, and corn.

8. A method of producing mature soybean seed β-ketoacyl-ACP synthetase II enzyme in microorganisms comprising:

(a) transforming a microorganism with a chimeric gene of claim 5, and (b) growing the transformed microorganism of step (a) to produce quantities of said mature soybean seed β-ketoacyl-ACP synthetase II enzyme.

9. A transformed plant having cells comprising a chimeric gene comprising a nucleic acid fragment of claim 1 operably linked so suitable heterologous regulatory sequences, the chimeric gene causing altered level of soybean seed β-ketoacyl-ACP synthase II in seed produce by the transformed plant.

10. Seed of the transformed plant of claim 9.

* * * * *